United States Patent [19]
Houck et al.

[11] Patent Number: 5,866,004
[45] Date of Patent: Feb. 2, 1999

[54] AUTOMATED SUPERCRITICAL FLUID EXTRACTION METHOD AND APPARATUS

[75] Inventors: Raymond K. Houck, Oakmont; Douglas J. Koebler, Irwin; Glen P. Williams, Springdale; Kenneth J. Kato, Export; Robert D. Parks, Pittsburgh; Paul A. Bauer, Jr., Brentwood, all of Pa.

[73] Assignee: Suprex Corporation, Pittsburgh, Pa.

[21] Appl. No.: 524,916

[22] Filed: Sep. 8, 1995

Related U.S. Application Data

[63] Continuation of Ser. No. 962,463, Oct. 16, 1992, abandoned.
[51] Int. Cl.⁶ .................................................. B01D 11/00
[52] U.S. Cl. ..................... 210/634; 210/136; 210/143; 210/180; 210/181; 210/511; 422/63; 422/64; 422/69; 422/102; 436/178
[58] Field of Search .................................. 210/634, 181, 210/136, 137, 656, 511, 198.2, 321.6, 143, 739, 180; 422/63, 64, 65, 69, 70, 101, 102; 436/178

[56] References Cited

U.S. PATENT DOCUMENTS

| | | | |
|---|---|---|---|
| 4,683,063 | 7/1987 | Rice | 210/634 |
| 4,814,089 | 3/1989 | Kumar . | |
| 4,892,654 | 1/1990 | Nickerson . | |
| 5,009,778 | 4/1991 | Nickerson et al. . | |
| 5,087,360 | 2/1992 | Wright et al. | 210/181 X |
| 5,094,741 | 3/1992 | Frank et al. . | |
| 5,094,753 | 3/1992 | Allington et al. . | |
| 5,132,014 | 7/1992 | Allington et al. . | |
| 5,133,859 | 7/1992 | Frank et al. . | |
| 5,151,178 | 9/1992 | Nickerson et al. . | |
| 5,151,188 | 9/1992 | Hopper et al. | 210/634 |
| 5,160,624 | 11/1992 | Clay et al. . | |
| 5,173,188 | 12/1992 | Winter et al. . | |
| 5,178,767 | 1/1993 | Nickerson et al. . | |
| 5,180,487 | 1/1993 | Saito et al. . | |
| 5,193,703 | 3/1993 | Staats et al. | 220/203 |
| 5,237,824 | 8/1993 | Pawliszyn | 62/51.1 |
| 5,260,028 | 11/1993 | Astle | 422/81 |
| 5,271,903 | 12/1993 | Durst et al. | 422/101 |
| 5,286,652 | 2/1994 | James et al. | 422/64 |

Primary Examiner—Joseph W. Drodge
Attorney, Agent, or Firm—Ansel M. Schwartz

[57] ABSTRACT

A supercritical fluid extraction (SFE) system. The SFE system includes a mechanism for providing supercritical fluid for extracting analyte from a sample. The SFE system also includes an extraction vessel and a mechanism for moving the extraction vessel into fluidic communication with the SFE system so that supercritical fluid can flow through the extraction vessel and extract analyte from the sample. Preferably, the SFE system is additionally comprised of a mechanism for holding a plurality of extraction vessels and an extraction chamber assembly. In this design, the moving mechanism selectively moves an extraction vessel from the holding mechanism into the extraction chamber in fluidic communication with the SFE system. Preferably, the SFE system further includes a computer for controlling the functions of the SFE system. The computer, for instance, could automatically and sequentially control the supercritical fluid extractions of the samples within the holding mechanism. The SFE system preferably includes a mechanism for collecting analyte from the fluid with analyte. The collecting mechanism is in fluid communication with extraction chamber assembly and preferably includes a restrictor for controlling the flow of fluid with analyte to the collecting mechanism. The restrictor converts the fluid with analyte from a first supercritical pressure to a second pressure which is less than the first supercritical pressure.

92 Claims, 24 Drawing Sheets

AUTOMATED SUPERCRITICAL FLUID EXTRACTION METHOD AND APPARATUS

This Application is a continuation of U.S. patent application Ser. No. 07/962,463, filed Oct. 16, 1992, now abandoned.

FIELD OF THE INVENTION

The present invention is related to supercritical fluid extraction. More specifically, the present invention is related to an automated supercritical fluid extraction and collection system.

BACKGROUND OF THE INVENTION

Supercritical fluid extraction (SFE) is a sample preparation technique used to extract analytes of interest from a sample, for example, environmental pollutants from a soil sample. Some type of sample preparation must be performed for a wide range of environmental, food, polymer, petroleum, pharmaceutical and other classes of samples due to the complex nature of the samples. Many of these samples are so complex that they cannot be directly analyzed by analytical techniques such as gas chromatography (GC) or liquid chromatography (LC). The complex samples must first go through a sample preparation step to perform a gross separation of the analytes of interest from the sample matrix in which they are contained, for example, the environmental pollutants from soil. After the sample preparation step, then just the analytes of interest are analyzed by the analytical technique such as gas chromatography (GC), liquid chromatography (LC), or supercritical fluid chromatography (SFC). Other analytical techniques could be used such as mass spectroscopy (MS) or nuclear magnetic resource (NMR).

The most popular sample preparation steps are Soxhlet extraction and liquid extraction. An alternative to these types of extraction techniques is supercritical fluid extraction (SFE). SFE offers a relatively rapid, simple and inexpensive technique to perform sample preparations. The basis of SFE is that a fluid, such as carbon dioxide, is held at a specific pressure, temperature and flowrate, which is above its critical temperature and pressure and thus is a supercritical fluid. The supercritical fluid is passed through the sample matrix containing the analytes of interest. This sample matrix is contained in an extraction vessel. The fluid diffuses into the pores of the matrix, solubilizes the analytes of interest, and then carries the analytes away from the matrix. The analytes are then collected by some device, so that the analytes can be analyzed by some further analytical technique, such as chromatography. The matrix (now without analytes) is left behind in the extraction vessel. Supercritical fluids have favorable diffusivities and viscosities providing for good mass transfer characteristics. Their solvent strength can be easily controlled by changing fluid pressure or temperature. These are but a few of the advantages of supercritical fluid extraction.

Typically, an SFE system is comprised of a pump which pumps the supercritical fluid to an extraction vessel where analytes are extracted from a sample matrix. The analytes are then transported to a collection device where the supercritical fluid is depressurized to ambient pressure and is vented. The analysis of the collected analytes can be either "off-line", that is, remote from the extraction and/or collection device, or "on-line", that is, fluidically connected to the extraction and/or collection device.

The primary supercritical fluid used in SFE is carbon dioxide due to its low pressure and temperature critical points (71 atm, 31° C., respectively) and its ability to solubilize nonpolar or moderately polar analytes. When it is desired to extract a polar analyte, then it is well known in the art to employ a co-solvent with the carbon dioxide. These co-solvents are typically referred to as modifiers or entrainers and are typically a liquid organic solvent such as methanol, ethanol, propylene carbonate, acetone, tetrahydrofuran, fomic acid, etc. that are blended with the carbon dioxide in 1 to 50% by volume or mole percent to form a mixture that retains much of the diffusion characteristics of the pure carbon dioxide phase but that has a much higher polarity and thus is able to solubilize polar analytes and extract the polar analytes from the sample matrix.

The prior art of SFE is quite large (see, for instance, U.S. Pat. No. 4,500,432, "Supercritical Fluid Technology", ACS Symposium Series 488, Chapter 12, McNally et al., 1991, pp. 144–164, "A Model for Dynamic Extraction Using Supercritical Fluid", Bartle et al., Journal of Supercritical Fluids", 1990, 3, 143–149, "Supercritical Fluid Extraction & Chromatography", ACS Symposium Series 366, Chapter 3, Wright et al., 1988, pp. 44–62, U.S. Pat. No. 4,597,943, European Patent No. 0444299A1, European Patent No. 0384969A2, European Patent No. 0458125A2, European Patent No. 0438184A1, U.S. Pat. No. 5,031,448, U.S. Pat. No. 5,013,443, U.S. Pat. No. 5,087,360, U.S. Pat. No. 4,984,602).

It has been generally known in the prior art that SFE must be automated to allow the technology to grow (see M. L. Bruce, "Beyond the Hype", August/September 1991, Environmental Lab). Only with a reliable, rapid, multisample analysis will the technique of supercritical fluid extraction be exploited to full advantage. One approach toward SFE automation is shown in "Supercritical Fluid Technology", ACS Symposium Series 488, Chapter 12, McNally et al., 1991, pp. 144–184. In this method, a series of extraction vessels (up to 12) are plumbed into a common rotary valve. The extraction vessels are not moved. The rotary valve is rotated to fluidically connect one of the extraction vessels to the plumbing of the extraction system. This relatively complex valve system is difficult to clean due to the numerous and essentially redundant fluid lines and is prone to leakage due to the rotary valve and the many plumbing fittings.

The basic needs of SFE are well known but the present invention has advantages over the prior art in a number of important areas including: 1) the ability to automate the SFE process so that it runs unattended for preferably up to 44 samples (or more); commensurate with 2) the ability to individually program each extraction vessel or fraction of a vessel with a different pressure, temperature, percent modifier, supercritical fluid flowrate and analyte collection method; and 3) the incorporation of a new variable restrictor that allows the effective decompression of the supercritical fluid into the collection system. The variable restrictor is unique due to its low dead volume, ability to control carbon dioxide flows in the 0.3 to 7.0 ml/min. range, and ability to keep the depressurized carbon dioxide from freezing in the outlet of the value.

SUMMARY OF THE INVENTION

The present invention is a supercritical fluid extraction (SFE) system. The SFE system comprises means for providing supercritical fluid for extracting analyte from a sample. The SFE system also comprises an extraction vessel and means for moving the extraction vessel into fluidic communication with the SFE system so that supercritical fluid can flow through the extraction vessel and extract analyte from the sample.

Preferably, the SFE system is additionally comprised of means for holding a plurality of extraction vessels and an extraction chamber assembly. In this design, the moving means selectively moves an extraction vessel from the holding means into the extraction chamber in fluidic communication with the SFE system. Preferably, the SFE system further includes a computer for controlling the functions of the SFE system. The computer, for instance, could automatically and sequentially control the supercritical fluid extractions of the samples within the holding means. The SFE system preferably includes means for collecting analyte from the fluid with analyte. The collecting means is in fluid communication with extraction chamber assembly and preferably includes a restrictor for controlling the flow of fluid with analyte to the collecting means. The restrictor converts the fluid with analyte from a first supercritical pressure to a second pressure which is less than the first supercritical pressure.

In a preferred embodiment, the moving means includes a mechanism for clamping an extraction vessel within the extraction chamber assembly such that the extraction vessel is disposed in fluidic communication between the providing means and the collecting means. Also, as shown in FIG. 2, the moving means includes means for presenting an extraction vessel from the holding means to the clamping mechanism. Preferably, the holding means is comprised of a carousel within which the plurality of extraction vessels are held and the presenting means includes a rotary table in contact with the carousel for turning the carousel to selectively present the extraction vessels to the clamping mechanism.

The extraction chamber assembly preferably includes means for heating the sample within an extraction vessel in the extraction chamber assembly and the plunger includes means for preheating the supercritical fluid as it flows therethrough.

In a first embodiment of the extraction chamber assembly, as shown in FIG. 3, the extraction vessels are adapted to withstand the pressure of the supercritical fluid and are thus mini pressure vessels. The extraction chamber assembly surrounds the extraction vessel but does not feel the pressure of the supercritical fluid. In a second embodiment, and as shown in FIG. 4, the extraction chamber assembly has pressure retaining means designed to withstand the pressure of the supercritical fluid in the extraction vessel within the extraction chamber assembly. In a third embodiment, and as shown in FIGS. 5a and 5b, the extraction chamber assembly has the pressure retaining means in a clamshell like construction.

The present invention is also a pumping system for providing supercritical fluid. The pumping system comprises an output from which supercritical fluid at a desired pressure and flowrate passes. The pumping system also comprises means for providing supercritical fluid to the output. The providing means is in fluidic communication with the output. The providing means has at least one variable speed piston which pressurizes the fluid. The speed of the piston at a given time corresponding to the pressure and flowrate of the fluid which passes from the output at the given time. The pumping system also comprises microprocessor control means for controlling the providing means such that the pressure and flowrate of the supercritical fluid provided by the output is maintained at a desired pressure and flowrate.

If desired, the heating means of the extraction chamber assembly and preheating means in the plunger can be combined into a single high power heating means. During the operation of the high power heating means, the incoming supercritical fluid (and modifier, if any) are heated to the extraction temperature conditions by the high power heating means. The supercritical fluid then essentially carries the heat into the extraction vessel that contains the sample matrix. The extraction chamber has a thermal insulation means which essentially prevents this heat from escaping and focuses the heat onto the matrix so that the heat utilization is efficient.

The SFE system prevents the volatization of analytes by providing a "closed" extraction vessel. The extraction vessel is "air tight" when sitting on the carousel and thus no volatile analytes can escape from the vessel. When the vessel is moved into position in the extraction chamber, the plunger and the end cap of the extraction chamber mechanism open the sealed extraction vessel.

In a first embodiment of the second extraction vessel, the extraction vessel is comprised of a container defining the chamber, a first end having a first opening in fluidic communication with the chamber and a second end having a second opening in fluid communication with the chamber. A first check valve is disposed on the first end of the container for selectively sealing the first opening from the chamber and a second check valve is disposed on the second end of the container for selectively sealing the second opening from the chamber. In a second embodiment, the extraction vessel is sealed with puncturable membranes.

The present invention also describes an extraction device. The extraction device comprises an insert for containing a sample during supercritical fluid extraction. The insert is retained within a container having a chamber. Preferably, the insert is porous and can be comprised of teflon material such as PTFE. Preferably, the liner is porous and thus does not have to be punctured during extraction. The supercritical fluid flows through the microscopic holes in the teflon to the sample to extract analyte, from the sample. The holes are small enough to prevent passage of the sample matrix therethrough.

The SFE system can include means for removing water from the supercritical fluid with analyte such as a second vessel filled with an absorbent such as sodium sulfate, magnesium sulfate or hydromatrix is installed immediately after the extraction vessel.

Preferably, the SFE system includes means, such as a computer, for controlling the flow of fluid from the providing means to the extraction vessel and to the collecting means such that any leaks or plugs are detected.

The present invention also describes a restrictor which is automatically controlled by the computer. The restrictor has a first port in fluidic communication with the extraction vessel, a second port in fluidic communication with the collecting means and a third port in fluidic communication with means for providing desorbing solvent to the collection means.

The SFE system preferably provides a vent valve V2 for venting supercritical fluid downstream from the extraction chamber. The vent valve V2 is located downstream of the extraction chamber. The vent valve V2 has a first path and a second path. The collecting means is in fluidic communication with the extraction vessel through the first path. The supercritical fluid is vented from the extraction vessel along the second path 118 through a vent.

The present invention is also a method for supercritical fluid extraction. The method comprises the steps of moving an extraction vessel having a sample with an automated moving device into fluidic communication with a supercritical fluid extraction system so that the supercritical fluid can flow through the extraction vessel and extract analyte from the sample. Then, there is the step of extracting analyte from the sample with supercritical fluid.

The present invention pertains to an extraction apparatus. The extraction apparatus comprises a mechanism for automatically performing supercritical fluid extraction on a series of samples one after the other without substantially handling the apparatus for supercritical fluid extraction between extractions. The mechanism for automatically performing supercritical fluid extractions includes an extraction chamber assembly having an interior, exterior and an orifice for introduction of samples, a first port for fluid entrance and at least a second port for a fluid outlet. The mechanism for automatically performing supercritical fluid extraction also includes a sample injector mechanism for automatically injecting into the extraction chamber assembly a series of samples from a storage apparatus for feeding samples in series and for extracting each sample prior to introducing the next sample. Additionally, there is a variable restrictor for reducing pressure of supercritical fluid after extraction has occurred in the extraction chamber assembly.

The present invention pertains to a method for supercritical fluid extraction of a sample. The method comprises the steps of extracting under supercritical conditions by automatically injecting a series of samples into an extraction chamber assembly having an interior, an exterior, an orifice for introducing of sample, a first port for fluid entrance and at least a second port for a fluid outlet. Next there is the step of extracting each sample prior to introducing a next sample with solvent at a supercritical pressure. Then there is the step of flowing the fluid at the supercritical pressure through a variable restrictor to reduce the pressure.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
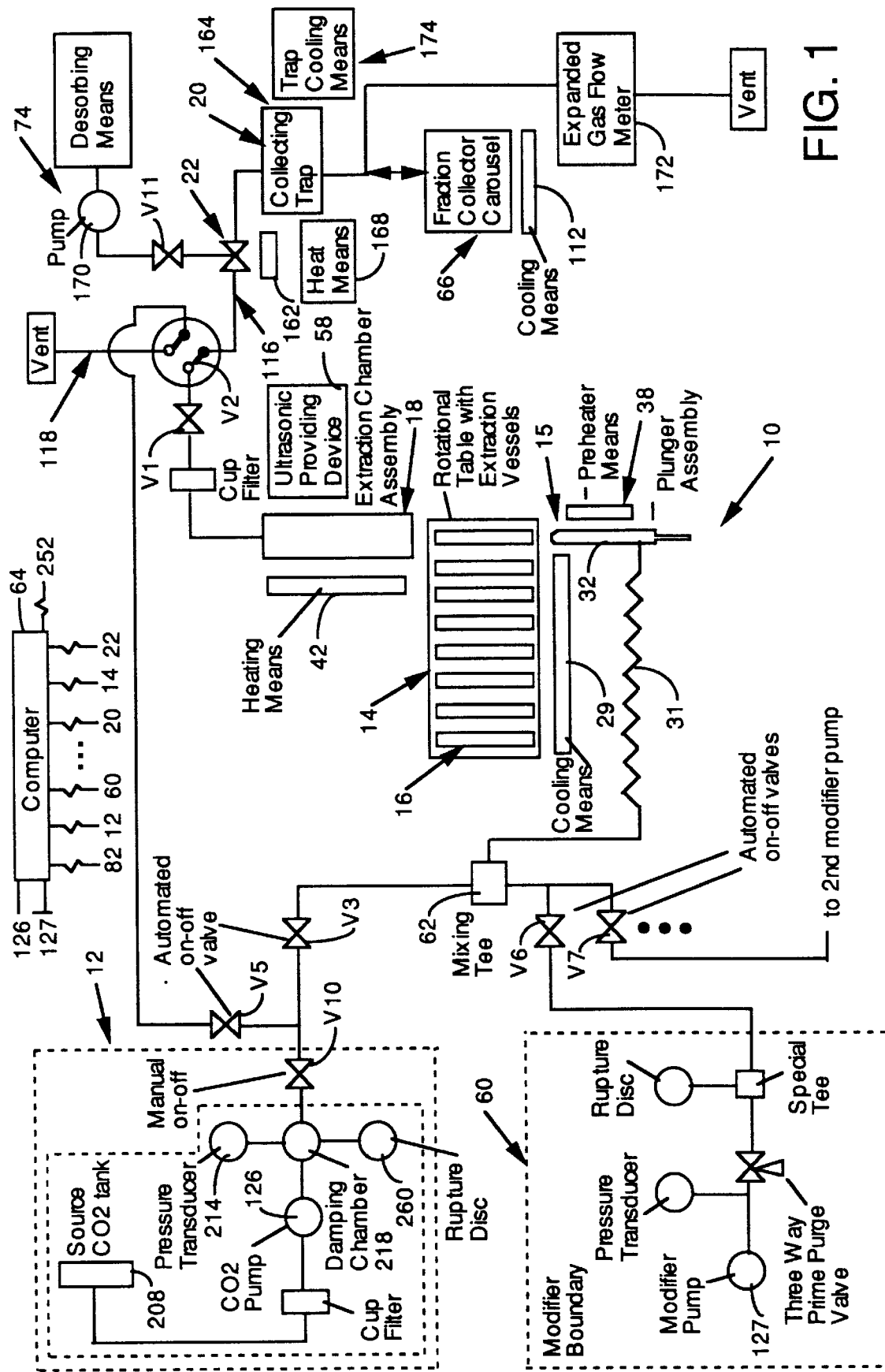
FIG. 1 is a schematic representation showing the supercritical fluid extraction system of the present invention.

Referring now to the drawings wherein like reference numerals refer to similar or identical parts throughout the several views, and more specifically to FIG. 1 thereof, there is shown a supercritical fluid extraction (SFE) system 10. The SFE system comprises means 12 for providing supercritical fluid for extracting analyte from a sample. The SFE system 10 also comprises an extraction vessel 16 and means 15 for moving the extraction vessel 16 into fluidic communication with the SFE system 10 so that supercritical fluid can flow through the extraction vessel 16 and extract analyte from the sample.

Preferably, the SFE system 10 is additionally comprised of means 14 for holding a plurality of extraction vessels 16 and an extraction chamber assembly 18. In this design, the moving means 15 selectively moves an extraction vessel 16 from the holding means 14 into the extraction chamber 18 in fluidic communication with the providing means 12.

Preferably, the SFE system 10 further includes a computer 64 for controlling the functions of the SFE system. The computer 64, for instance, could automatically and sequentially control the supercritical fluid extractions of the samples within the holding means 14.

The SFE system 10 preferably includes means 20 for collecting analyte from the fluid with analyte. The collecting means 20 is in fluid communication with extraction chamber assembly 18 and preferably includes a restrictor 22 for controlling the flow of fluid with analyte to the collecting means 20. The restrictor 22 converts the fluid with analyte from a first supercritical pressure to a second pressure which is less than the first supercritical pressure.

Figure 2:
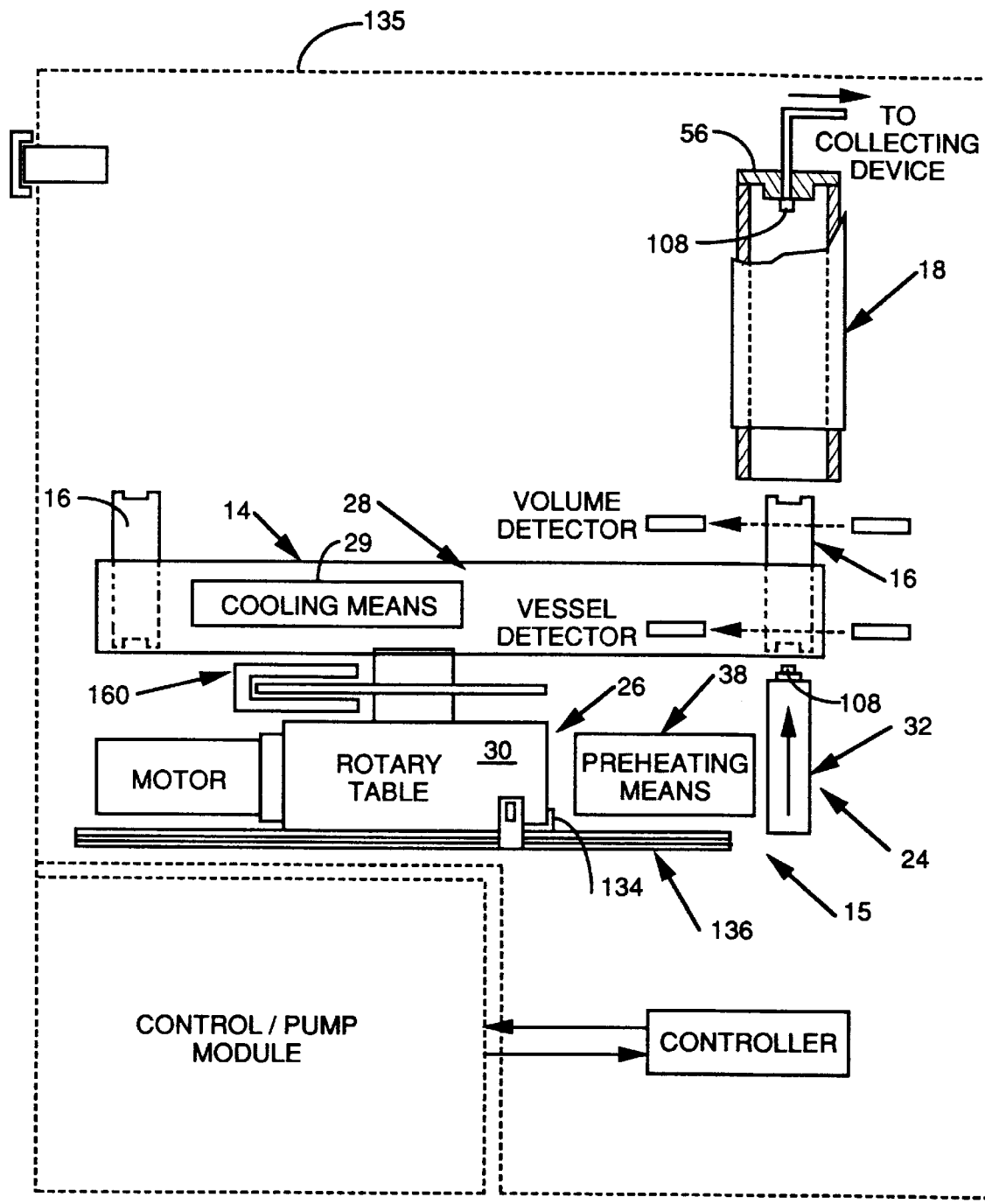
FIG. 2 is a schematic representation showing the extraction vessel holding means, the extracting vessel clamping means and the extraction vessel presenting means.
Figure 3:
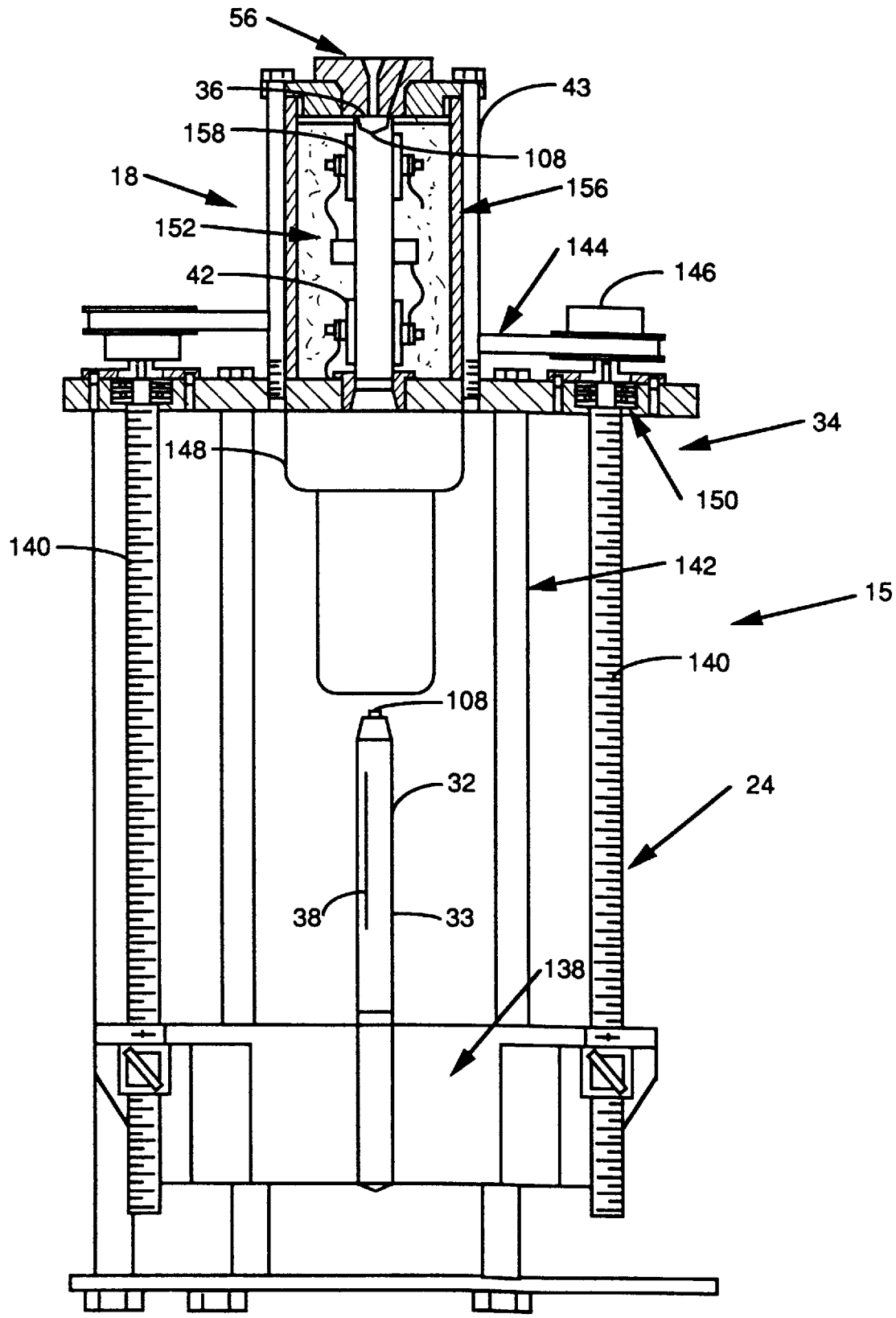
FIG. 3 is a schematic representation showing a first embodiment of the extraction chamber assembly and plunger assembly.

In a preferred embodiment and as shown in FIG. 3, the moving means 15 includes a mechanism 24 for clamping an extraction vessel 16 within the extraction chamber assembly 18 such that the extraction vessel 16 is disposed in fluidic communication between the providing means 12 and the collecting means 20. Also, as shown in FIG. 2, the moving means 15 includes means 26 for presenting an extraction vessel 16 from the holding means 14 to the clamping mechanism 24. Preferably, the holding means 14 is comprised of a carousel 28 within which the plurality of extraction vessels 16 are held and the presenting means 24 includes a rotary table 30 in contact with the carousel 28 for turning the carousel 28 to selectively present the extraction vessels 16 to the clamping mechanism 24. It should be noted that the moving means can also be a robotic arm or a piston type mechanism.

Referring to FIGS. 1, 2 and 3, preferably, the clamping mechanism 24 includes a plunger 32 in fluidic communication with the supercritical fluid providing means 12. The clamping mechanism 24 is also comprised of means 34 for driving the plunger 32 such that an extraction vessel 16 presented to the plunger 32 by the presenting means 26 can be pushed from the carousel 28 by the plunger 32 into the extraction chamber assembly 18 for supercritical fluid extraction, as shown in FIG. 3. Preferably, the providing means 12 comprises a coiled tube 31, as shown in FIG. 1, which provides flexibility as the plunger 32 is displaced by the driving means 34. Supercritical fluid is forced through the coiled tube into an internal channel 33 within the plunger 32. The supercritical fluid flows from the internal channel 33 into the extraction vessel 16 when the extraction vessel 16 is properly positioned in the extraction chamber assembly 18. Preferably, there is means 36 for sensing when a selected extraction vessel 16 is in proper engagement within the extraction chamber assembly 18. The sensing means 36 can be a contact sensor or force sensor connected to the computer 64. The control sensor is disposed at the top of the extraction chamber assembly 18 and sends a signal to the computer 64 when the vessel 16 is properly seated. Alternatively, a force sensor could sense the force exerted by plunger 32 on vessel 16 and then computer 64 could determine if vessel 16 was properly engaged within extraction chamber 18.

The extraction chamber assembly 18 preferably includes means 42 for heating the sample within an extraction vessel 16 in the extraction chamber assembly 18 and the plunger 32 includes means 38 for preheating the supercritical fluid as it flows therethrough. The preheating means 38 preferably includes a cartridge heater to provide heat to the fluid, an RTD to sense the heat, and a length of 0.030 inch ID stainless steel tubing which is wrapped around a steel block containing the cartridge heater and RTD. The cartridge heater heats the block which in turn heats the coil of tubing that the supercritical fluid passes through, thus the fluid is, in turn heated. The RTD senses the temperature and feeds its information to computer 64, which then, in turn, controls the current going to the cartridge heater.

In a first embodiment of the extraction chamber assembly 18, as shown in FIG. 3, the extraction vessels 16 are adapted to withstand the pressure of the supercritical fluid and are thus mini pressure vessels. The extraction chamber assembly 18 surrounds the extraction vessel 16 but does not feel the pressure of the supercritical fluid in the extraction vessel 16 therein.

Figure 4:
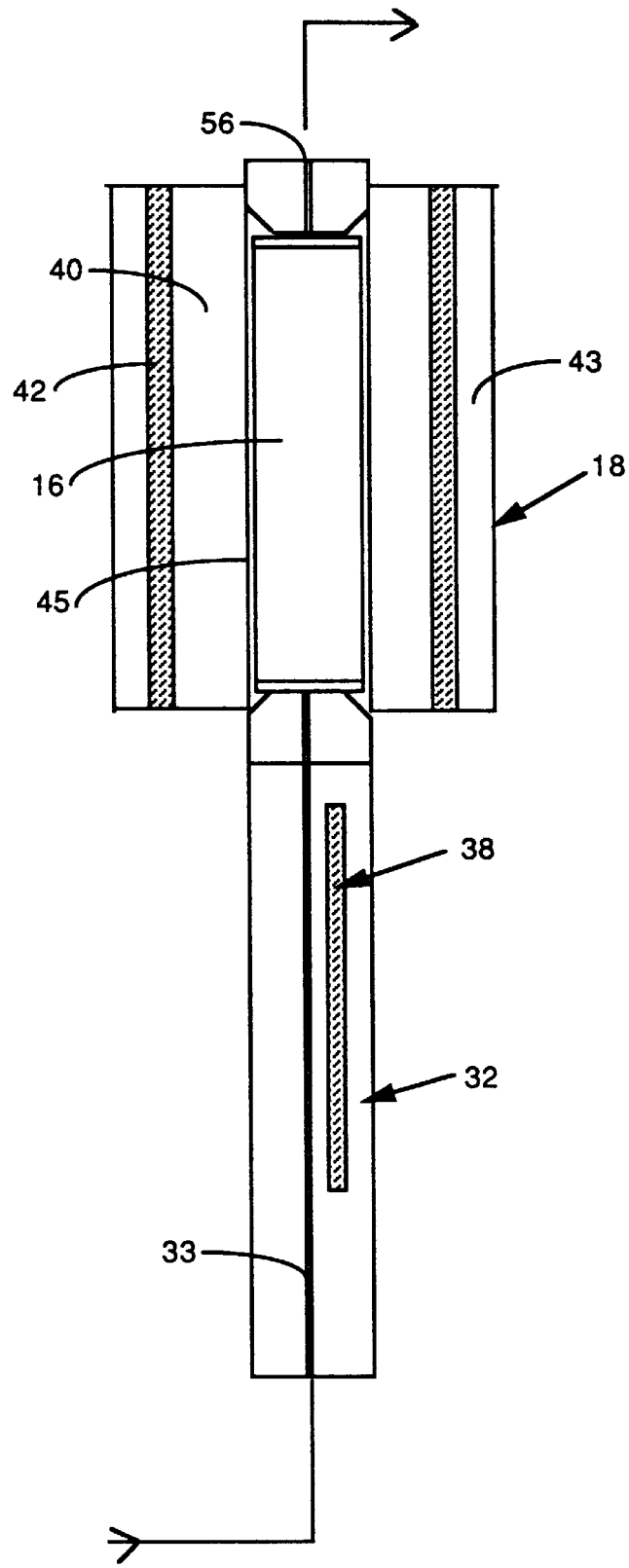
FIG. 4 is a schematic representation showing a second embodiment of the extraction chamber assembly.

In a second embodiment, and as shown in FIG. 4, the extraction chamber assembly 18 has pressure retaining means 40 designed to withstand the pressure of the supercritical fluid in the extraction vessel 16 within the extraction chamber assembly 18. For instance, the pressure retaining means 40 is a stainless steel cylinder having sufficient wall thickness to support the pressure of the supercritical fluid which can be as high as 680 atm or higher. In this embodiment, during extraction, the pressure of the supercritical fluid is transferred through the walls of the vessel 16 against the pressure retaining means 40 built into the extraction chamber assembly 18. Thus, the extraction vessel 16 does not need to have the structural integrity necessary to withstand supercritical pressures. In addition, end cap 56 and plunger 32 must also have this pressure retaining ability as they also do in the first embodiment. The advantage of this approach is that since the pressure retaining means 40 is in the extraction chamber assembly 18, the extraction vessel 16 can be constructed inexpensively, from low pressure materials such as thin walled stainless steel, poly-ether-ether-ketone (PEEK) or other high performance, low extractable plastic or composite material. Preferably, the extraction chamber assembly 18 has a housing 43.

In the second embodiment of the extraction chamber assembly 18, the extraction vessel 16 is of a size, or can expand to a size which effectively conforms with the inner wall 45 so the pressure within can be transferred to the pressure retaining means 40, and not explode the walls of the vessel 16. The vessel 16 must be rigid enough that it does not bind to the inner wall 45 of the extraction chamber 18, so gravity alone can cause the extraction vessel 16 to withdraw from the extraction chamber 18 as the plunger 32 travels downward. An alternative is to have a spring in the top of the extraction chamber to give the vessel 16 an added push as the plunger travels downward.

Figure 5B:
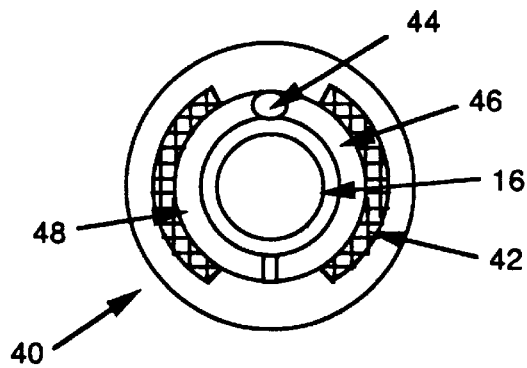
FIGS. 5a and 5b are schematic representations showing a third embodiment of the extraction chamber assembly.
Figure 5A:
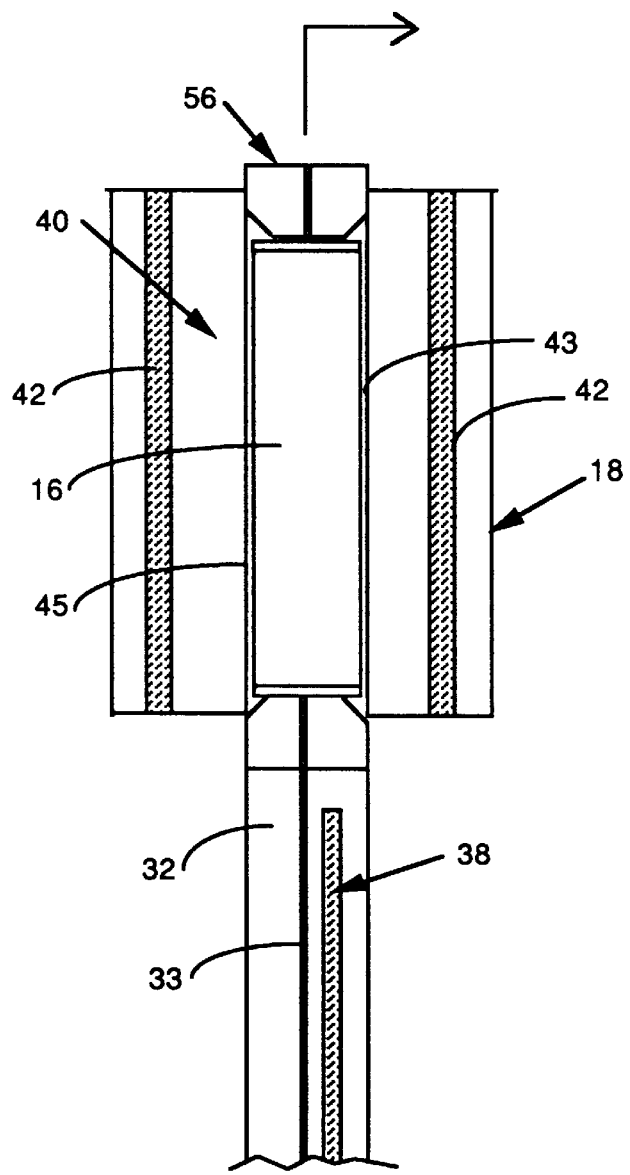

In a third embodiment, and as shown in FIG. 5a and 5b, the extraction chamber assembly 18 has the pressure retaining means 40 in a clamshell like construction. The pressure retaining means 40 holds up to 680 atm and consists of a hinge 44 that connects two halves 46, 48 of the pressure retaining means 40. The two halves clamp together to form a closed pressure chamber 43 which holds the vessel 16 when they are in contact, and releases the vessel 16 when they are not in contact. The closed pressure chamber 37 is capable of containing up to 680 atm of pressure. Preferably, there is a hydraulic or motor driver system that clamps the two halves 46, 48 together, much like the action of a "C" clamp so that the two halves 46, 48 hold the system pressure of up to 680 atm.

The advantage of this third embodiment is that a soft material can be used for the construction of the extraction vessel 16; or a very thin walled vessel can be used for the extraction vessel 16 made from stainless steel or poly-either-ether-ketone or some other high performance plastic, composite or paper. Additionally, the extraction vessel 16 can be placed sideways or vertically into the chamber assembly 18. The vessel 16 in this embodiment, as in the second, can withstand up to 50 atm of pressure and preferably 4–7 atm of pressure but can be as low as 2–3 atm of pressure relative to the external pressure.

In the third embodiment of the extraction chamber assembly 18, the rigid structure constraint of the second embodiment is relaxed due to the clamshell design. The extraction vessel 16 does not have to be so rigid and can be made of thinner wall material. If the extraction vessel 16 does conform to the inner wall 45 of the extraction chamber 18, to withdraw the extraction vessel 16 from the chamber 18, the clamshell would open up, thus unbinding the extraction vessel 16 from the inner wall 45. Then the plunger 32 would travel downward away from the chamber assembly 18. Thus, the extraction vessel 16 would withdraw from the extraction chamber 18 even if it was physically bound to the inner wall 45 of the extraction chamber 18 during the pressurization and extraction phase of the process.

Figure 14A:
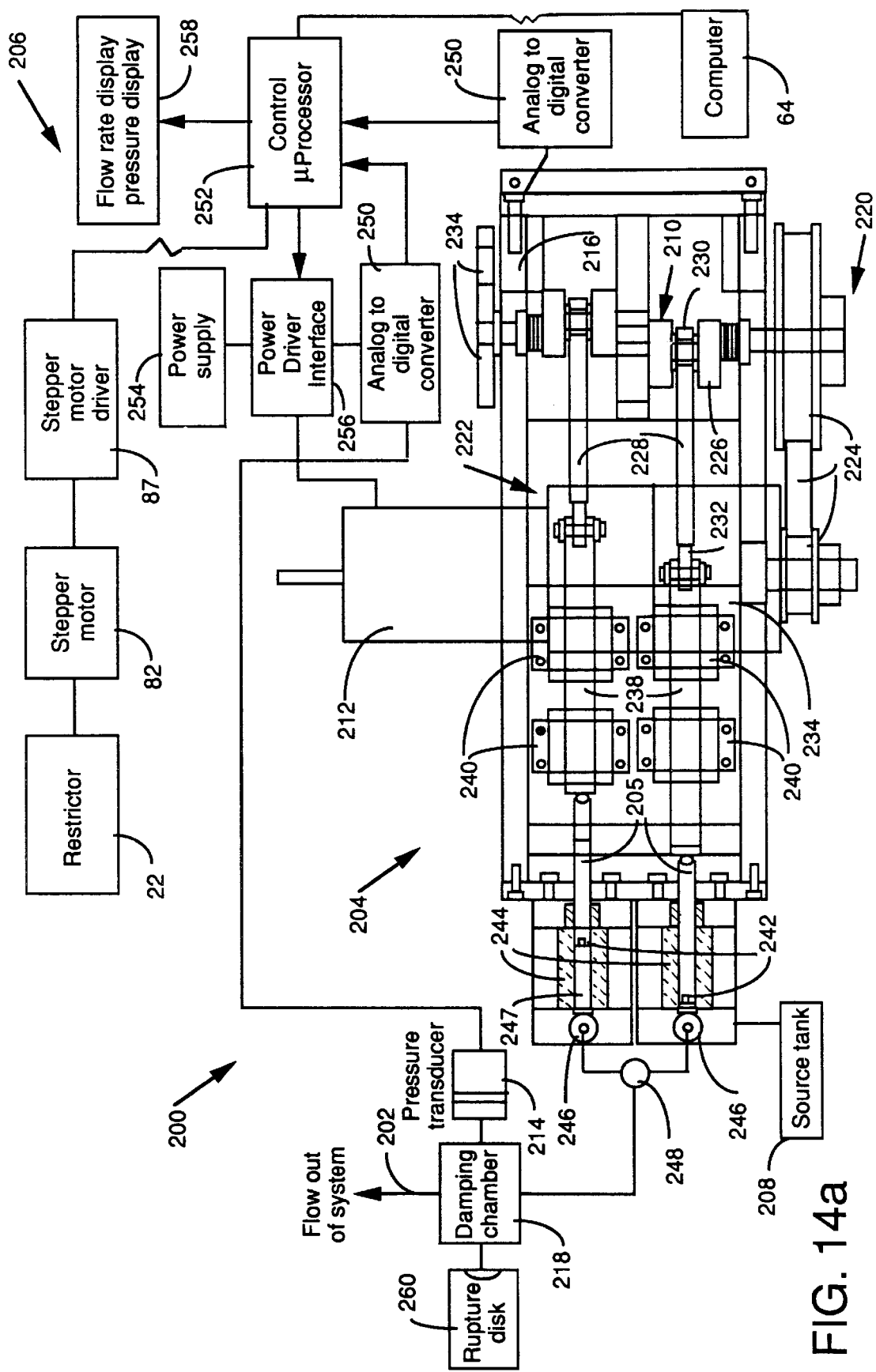
FIGS. 14a and 14b are schematic representation of the pumping system.
Figure 14B:
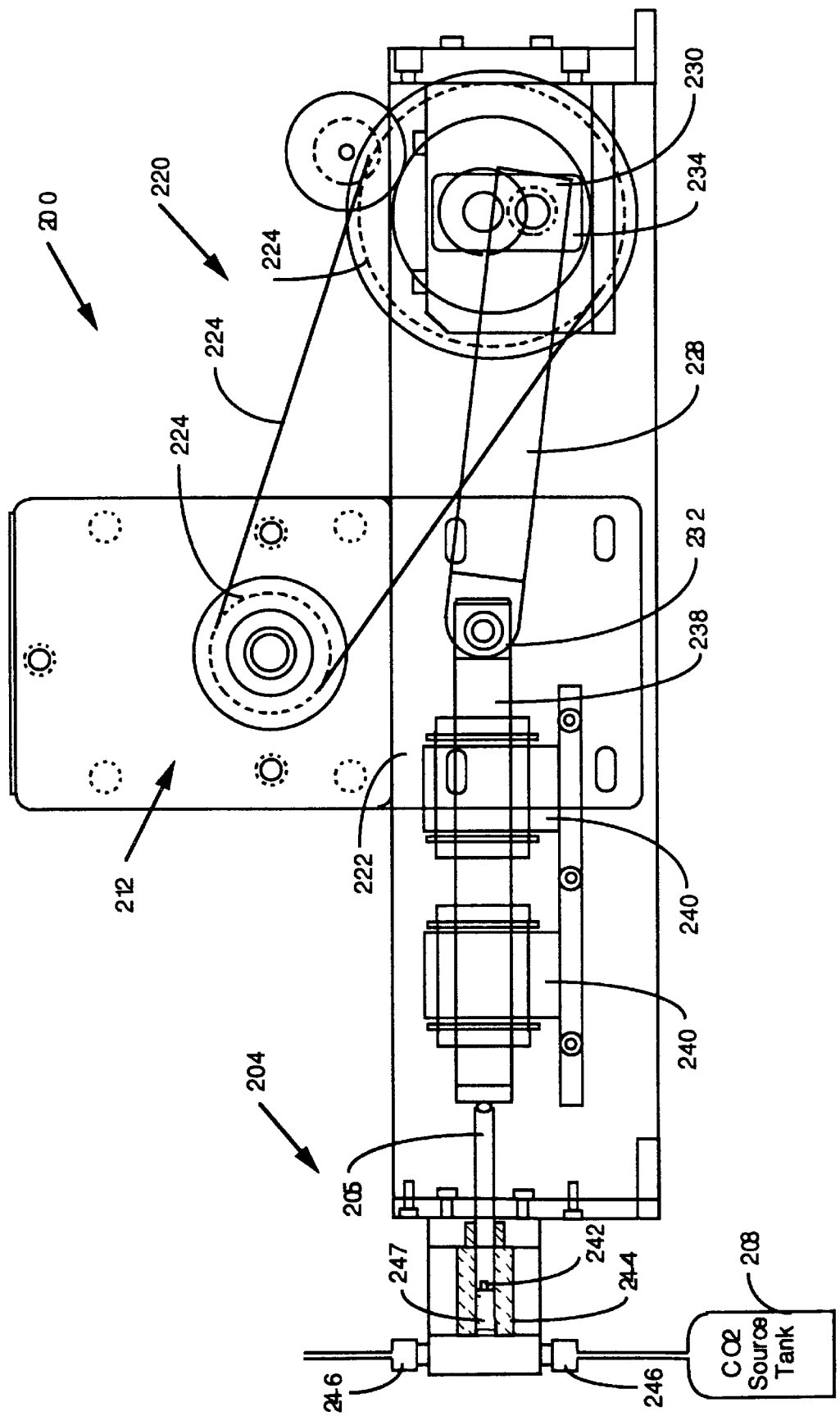

As shown in FIGS. 14a and 14b, the present invention is also a pumping system 200 for providing supercritical fluid. The pumping system 200 comprises an output 202 from which supercritical fluid at a desired pressure and flowrate passes. The pumping system also comprises means 204 for providing supercritical fluid to the output 202. The providing means 204 is in fluidic communication with the output 202. The providing means has at least one variable speed piston 205 which pressurizes the fluid. The speed of the piston 205 at a given time corresponds to the pressure and flowrate of the fluid which passes from the output 202 at the given time. The pumping system 200 also comprises microprocessor control means 206 for controlling the providing means 204 such that the pressure and flowrate of the supercritical fluid provided by the output 202 is maintained at a desired pressure and flowrate. In a preferred embodiment, the providing means 204 includes a source tank 208, a pump assembly 210 having the piston 205 in fluidic communication with the source tank 208 and a motor 212 for driving the piston 205. The motor has a variable power input which is controlled by the microprocessor control means 206. The microprocessor control means 206 includes a pressure transducer 214 for measuring the pressure of the supercritical fluid at the output 202 and the microprocessor control means 206 comprises a piston position potentiometer 216. The output 202 comprises a damping chamber 218 which maintains the fluid passing therefrom essentially at a constant pressure.

Preferably, the pump assembly 210 comprises means 220 for providing rotary motion, and means 222 for converting the rotary motion into linear motion to drive the piston 205. Preferably, the rotary motion providing means 220 comprises a belt and pully system 224 connected to the motor 212 and a crankshaft 226 connected to the belt and pulley system 224. Preferably, the means for converting the rotary motion into linear motion 222 comprises a crankarm 228 which is connected to the crankshaft 226 at a first end 230 and which is connected to pushrods 238 at a second end 232.

Rotary output from DC motor 212 is directly coupled into gear reducer 234. The gear reducer 234 decreases the speed and increases the torque of the rotary output from DC motor 212. The output of gear reducer 234 is coupled to the crankshaft 226 through the belt and pulley system 224. The belt and pulley system 224 provides additional speed reduction and torque increase. A gear system 236 translates the angular position of the crankshaft 226 to the piston position potentiometer 216. The gear system 234 preferably has an exact 2 to 1 gear ratio. Thus, each 180 degree rotation of the crankshaft 226 causes a 360 degree rotation of the piston position potentiometer 216. The crankarms 228 translate the rotary motion of the crankshaft 226 to a linear motion of push rods 238. Four stationary linear bearings 240 ensure that the motion of the push rods 238 remains linear despite the vertical forces translated from the crankshaft 226 through the crankarms 228. The push rods 238 in turn impart force to the piston 205. The crankshaft 226 is constructed so that the motions of the two piston 205 are exactly 180 degrees out of phase. Therefore, one piston 205 will be moving forward while the other is moving backwards. Piston seals 242 make a gas and fluid tight seal with piston head liners 244. This prevents leaks of the fluid or gas being pumped. Paired inlet and outlet check valves 246 ensure that fluid may only be drawn from the source tank 208 and no fluid will be pumped back into the source tank 208.

Pumping action of the pumping system 200 occurs as a two phase process. In the first phase, the piston rod 205 is being withdrawn from the piston head liner 244. This causes a relative reduction in pressure within the pump head 247 and fluid is drawn into the pump head 247 through the inlet check valve 246. In the second phase, the piston 205 is pushed forward into the piston head liner 244. This causes the pressure to rise within the pump head 247. When the pressure in the pump head 247 exceeds the pressure in the damping chamber 218, the outlet check valve 246 opens and pressurized fluid flows from the pump head 247 into the damping chamber 218. A plumbing tee 248 allows delivery of fluid from whichever pump head 247 is currently in its second phase.

The damping chamber 218 is a reservoir of pressurized fluid used to reduce the pressure fluctuations seen by the output of the pumping system 200. A rupture disc 260 is provided in fluidic communication with the damping chamber 218 as a mechanical safety override for possible over pressurization of the pumping system 200. The pressure transducer 214 converts the pressure in the damping chamber 218 to a voltage. The output voltage of the pressure transducer 214 is converted to digital form by an analog to digital converter 250 and subsequently supplied to a control microprocessor 252. Similarly, the analog to digital converter 250 takes output from the piston position potentiometer 216 and converts it to digital form for the control microprocessor 252. There is a direct mathematical correlation between the crank shaft 226 angular position as read by the piston position potentiometer 216 and the linear position of the pistons 205. Thus, by applying the proper corrective formula the control microprocessor 252 can determine the linear position of either of the pistons 205. A regulated DC power supply 254 provides a source of energy that may be gated to the DC motor 212 via a power drive interface 256. The gating action of the power drive interface 256 is under direct and high speed control of the control microprocessor 252. Thus, the control microprocessor 252 can very rapidly apply and remove power from the DC motor 212. Finally, the control microprocessor 252 can write information for the user to read on a display panel 258. It should be noted that the pump system 200 does not require cooling.

The control method of the pumping system 200 is described as follows. Assume some flowrate out of the pumping system 200 called the actual flowrate. Define a desired delivery pressure called the set pressure. Define the pressure read by the control microprocessor 252 via the pressure transducer 214 as the actual pressure. Define the flowrate displayed on the display panel 258 as the estimated flowrate. The control algorithm stored in the control microprocessor 252 must maintain the actual pressure as close as possible to the set pressure while displaying an estimated flowrate as close as possible to the actual flowrate.

In order to maintain a constant pressure within the damping chamber any fluid that exits from the damping chamber 218 must be replaced by an equal amount of fluid delivered from one of the pump heads. It must be noted that this is only true if the temperature of the compressed fluid remains constant throughout the system. The impact of temperature changes will be explored later, assume for the moment that the temperature remains constant.

As fluid flows out of the pumping system, the pressure within the damping chamber 218 begins to drop. This pressure drop is sensed by the pressure transducer 214 and the information is received by the control microprocessor 252. If an appropriate amount of power can be delivered to the DC motor 212, then whichever piston 205 is currently in compression will move forward and deliver enough fluid to restore the pressure in the damping chamber 218. If the difference between the set pressure and the actual pressure is used to determine the proper power to apply to the DC motor 212 in a continuous control loop then whichever piston 205 is moving forward will be pumping fluid at the same rate as the actual flowrate. In reality, the control loop is not continuous. The pressure is sampled and any noise is filtered out over a discrete time interval called the sample time. The power sent to the DC motor 212 remains constant during any given sample time. The power sent to the DC motor 212 is changed at the beginning of the next sample time based on the actual pressure recorded during the previous sample time. By keeping the sample time very short as compared with the mechanical reaction time of the pumping system 200, one can closely approximate the continuous control loop discussed earlier. Thus by using pressure feedback to control the power output to the DC motor 212 the forward motion of the piston 205 that is currently supplying supercritical fluid will match the actual flowrate. The rate of motion of either piston 205 can be accurately determined by reading the piston position potentiometer 216 and linearizing its output. The control microprocessor 252 can accurately determine time intervals using a quartz crystal as a time base. Therefore, an accurate estimated flowrate may be calculated by dividing the volume displaced by the pistons 205 that is supplying supercritical liquid by the time interval over which the fluid is being supplied.

Since control of the actual pressure is not perfect the forward motion of the piston rod 205 will not exactly match the actual flowrate. However, if the actual pressure remains close to the set pressure then the average motion of the pistons 205 will closely match the actual flowrate. Therefore, if an average piston position is taken over a suitably long time interval the estimated flowrate can be determined to a high degree of accuracy even in the presence of short term pressure errors. By using such an averaging technique the error on the estimated flowrate may be controlled at the expense of a slower overall response to changes in the actual flowrate.

Fundamental to the above control methodology is the assumption that the power output to the DC motor 212 can be changed. Variable power is delivered to the DC motor 212 as described in the following. A control interval time is chosen to coincide with the sample time described in the preceding section. This control interval time was further divided into 128 smaller time intervals called ticks. In order to set the power output to the DC motor 212 the power driver interface 256 is commanded to gate power from the DC power supply 254 to the DC motor for a fixed number of ticks during any control interval time. By changing the number of ticks that power is supplied during a control interval time the average amount of power to the DC motor 212 may be increased or decreased. In addition the power delivery is made smoother by distributing the ticks during which the power is supplied evenly amongst the ticks during which no power is supplied. This reduces the velocity changes that occur in the output of the DC motor 212 to a minimum thus resulting in better pressure control.

As stated earlier the assumption of constant temperature in the pumping system 200 is not totally accurate. Fluid is supplied into the piston head liner 244 at the temperature of the source tank 208. The fluid becomes heated during its compression from the pressure at which it arrived from the source tank 208 to the set pressure. The rise in temperature of the fluid within the piston head liner 244 causes its density to be reduced. The difference in density of the fluid in the warm piston head liner 244 to the density of the fluid in the cooler damping chamber 218 causes a difference in the actual flowrate as compared with the forward motion the pistons 205. This difference results in higher than expected estimated flowrates. By experimentally determining the magnitude of the flowrate error due to temperature effects an algorithm can be devised to compensate for these errors. The application of this temperature compensation can significantly increase the accuracy of the flowrate estimates. These flowrate estimates can then be used as the basis for the control of restrictor 22. The control of restrictor 22 is based upon a control algorithm that uses the estimated actual flowrate from the pump and compares it to the set flowrate programmed by the user. The supercritical fluid provided by the pumping system 200 is used to extract analyte from the sample within the extraction vessel 16.

Figure 6:
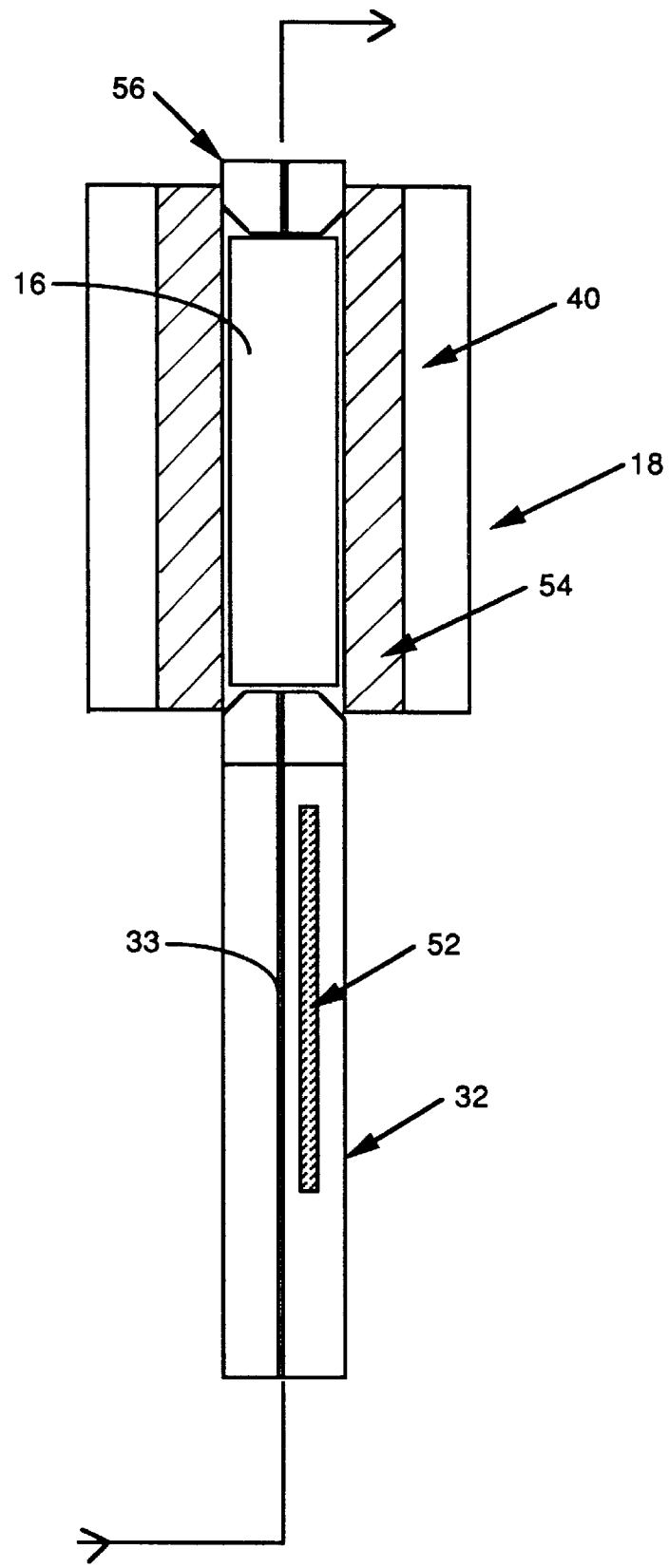
FIG. 6 is a schematic representation showing high power supercritical fluid heating means.

With respect to heating of the sample and supercritical fluid during extraction, if desired, as shown in FIG. 6, the heating means 42 of the extraction chamber assembly 18 and preheating means 38 in the plunger can be combined into a single high power heating means 52 contained in the plunger 32 (or near the inlet to the extraction chamber 18). In this design, the extraction chamber 18 consists of a thermal insulation section 54 made of ceramic or some type of thermal insulation material and a section that is the pressure retaining means 40 made from stainless steel. It should be noted that there are some ceramic, high performance plastic, and composite materials that can combine the pressure retaining means 40 and the thermal insulation 54 into one material, such as poly-ether-ether-ketone (PEEK), PEEK-graphite composite, liquid crystal polymers such as Vectra™ by Celanese Corporation, or Zirconia ($ZrO_2$), a ceramic material.

The design of the extraction chamber assembly 18 for use with the high power heating means 52 can be made with either the extraction chamber 18 having continuously round walls as previously described in the second embodiment of the extraction chamber assembly 18 or the clamshell design as previously described in the third embodiment of the extraction chamber assembly 18.

During the operation of the high power heating means 52, the incoming supercritical fluid (and modifier, if any) are heated to the extraction temperature conditions by the high power heating means 52. The supercritical fluid then essentially carries the heat into the extraction vessel 16 that contains the sample matrix. In this manner, the supercritical fluid itself heats up the sample matrix to the set conditions of the extraction. Preferably, the extraction vessel 16, the plunger 32 and the plug 56 of the extraction chamber assembly 18 which mates with the extraction vessel 16 are made from a material of low thermal conductivity such as stainless steel, poly-ether-ether-ketone (PEEK) or some other low thermal conductivity plastic or composite. In this manner, the majority of the heat is imparted into the sample matrix to heat the sample matrix (with analytes) to the extraction temperature set condition. Thus, very little heat is absorbed by the extraction vessel 16 or by the extraction chamber assembly 18.

Figure 7:
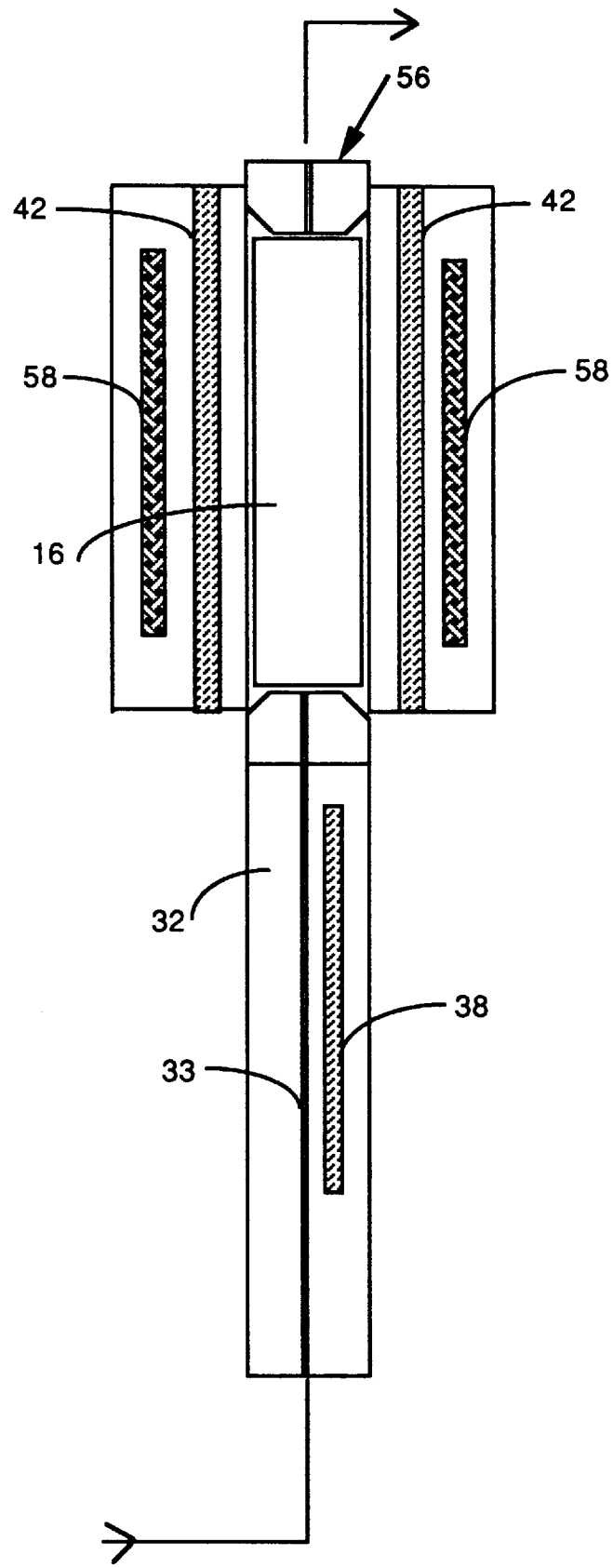
FIG. 7 is a schematic representation showing the extraction chamber assembly having means for providing ultrasonic energy.

To improve the extraction process, as shown in FIG. 7, the extraction chamber assembly 18 can include means 58 for providing ultrasonic energy to the sample within the extraction vessel 16. The diffusion coefficient of the supercritical fluid is gas-like ($10^{-3}$ to $^{-4}$ gm cm$^{-1}$ sec$^{-1}$) and thus SFE has its extraction in a fast time frame advantage. Still, SFE tends to be diffusion limited (K. D. Bartle, A. A. Clifford, S. B. Hawthorne, J. J. Langenfeld, D. J. Miller, R. Robinson, "A Model for Dynamic Extraction Using a Supercritical Fluid", Journal of Supercritical Fluids, Vol. 3, 1990, P. 143–149).

The application of ultrasonic energy to the extraction vessel 16 can speed up the diffusion of an analyte out of the interior of the sample to the surface of the pore structure of the sample where it can be solubilized by the supercritical fluid. Even though the supercritical fluid has good diffusion coefficients to diffuse into the pore structure of the matrix, this added ultrasonic energy from, for instance, a 20 kHz high power ultrasonic horn such as Bransen W-350 sonifier with a 102 converter, speeds up the extraction even more. (Further information on the use of ultrasonic energy to increase diffusion can be found in Bob W. Wright, J. L. Fulton, A. J. Kopriua, R. D. Smith, Analytical Supercritical Fluid Extraction Methodologies, Chapter 3 in book, "Supercritical Fluid Extraction and Chromatography", ACS Symposium Series 366, Editor: B. A. Carpentier, M. R. Sevenants, 1988, American Chemical Society, incorporated by reference.)

The present invention also recognizes that many types of samples, especially environmental samples, have volatile analytes that will volatize from the sample matrix and diffuse into the air. Thus, when analytizing these types of samples, these volatile analytes must be contained within the matrix and not be allowed to escape. The SFE system 10 prevents the volatization of analytes by providing a "closed" extraction vessel. The extraction vessel 16 is "air tight" when sitting on the carousel 28 and thus no volatile analytes can escape from the vessel 16. When the vessel 16 is moved into position in the extraction chamber 18, the plunger 23 and the end cap 56 of the extraction chamber 18 mechanism open the sealed extraction vessel 16 as described below. This allows the supercritical fluid to flow into the vessel 16 to extract the volatile and non-volatile analytes that are contained in the sample matrix and then allows the supercritical fluid containing the extracted analytes to exit from the vessel.

In a first embodiment of the extraction vessel 16 having a sealed chamber 84 for holding the sample matrix, and as shown in FIGS. 9a–9d, the extraction vessel 16 is comprised of a container 86 defining the chamber 84, a first end 88 having a first opening 90 in fluidic communication with the chamber 84 and a second end 92 having a second opening 94 in fluid communication with the chamber 84. A first check valve 96 is disposed on the first end 88 of the container 86 for selectively sealing the first opening 90 from the chamber 84 and a second check valve 98 is disposed on the second end 92 of the container 86 for selectively sealing the second opening 94 from the chamber 84. Preferably, the check valves 96 and 98 are comprised of a seal portion 100 and a spring portion 102 for biasing the seal portion 100 against the respective opening 90, 94. Preferably, each end 88, 92 of the container 86 has a seal member 103, which can be comprised of PEEK, and a porous frit 106. The spring portion 102 rests against the frit 106 and biases the seal portion 100 outward against the opening 90, 94 in the seal member 103, respectively.

During operation of the extraction vessel 16 with check valve seals 96, 98, when the extraction vessel 16 is in the carousel 28, the check valves 96, 98 form an airtight seal to prevent volatile analytes from escaping. When the extraction vessel 16 is moved into position between the plunger 32 and the end cap 56 in the extraction chamber assembly 18, a small nipple 108 on both the end cap 56 and the plunger 32 push the seal portion 100 from the first and second openings 90, 94, respectively, so that a fluid flow channel is opened such that supercritical fluid can flow from the internal channel 33 of the plunger 32 into the extraction vessel 16 and dissolved analytes in the fluid can flow out of the extraction vessel 16. It should be noted that this check valve design is reusable a number of times.

In FIGS. 10a–10d, a second embodiment of the extraction vessel 16 with a sealed chamber 84 is shown. In this embodiment, a non-porous membrane 110 made from Teflon, PEEK or similar non-porous and non-extractable plastic is positioned over either opening 90, 94 of the extraction vessel 16. Thus, the extraction vessel 16 is sealed when in the carousel 28 and volatile analytes cannot escape. When the extraction vessel 16 is moved into the extraction chamber assembly 18, the nipple 108 on the plunger 32 and on the end cap 56 pierces the membranes 110 to open the sealed chamber 84. This allows the flow of fluid into the vessel 16 and fluid and dissolved analytes out of the vessel 16. Preferably, the membranes 110 have a plurality of channels 114 formed therein which fracture during puncturing to break the membrane 110 in an orderly fashion.

Especially in environmental samples, there are a number of analytes that can thermally degrade and/or biological action in the sample can occur if the sample is kept at room temperature. Thus, it is desirable in certain applications to cool the extraction vessel carousel 28 and the fraction collector carousel 66 to as low as 4° C. to prevent this thermal degradation and/or biological activity to occur. Accordingly, cooling means 29, as shown in FIG. 2, and cooling unit 112, as shown in FIG. 1, such as $CO_2$ or glycol/water cooling units, are provided adjacent to and in thermal communication with the extraction vessel carousel 28 and the fraction collector carousel 66, respectively. This cooling decreases the vapor pressure of the analytes in the sample matrix and thus acts to keep the volatile analytes in the sample or a vial from volatizing and diffusing into the air. The cooling means 29 and cooling unit 112 supplement the closed extraction vessel feature previously described.

Figure 12A:
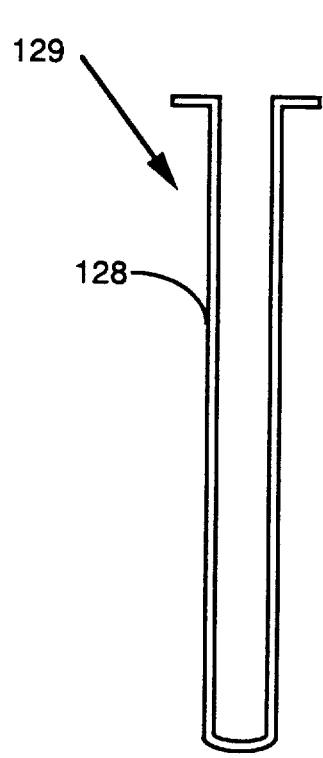
FIG. 12a FIG. 12b are schematic representations showing the extraction vessel liner.
Figure 12B:
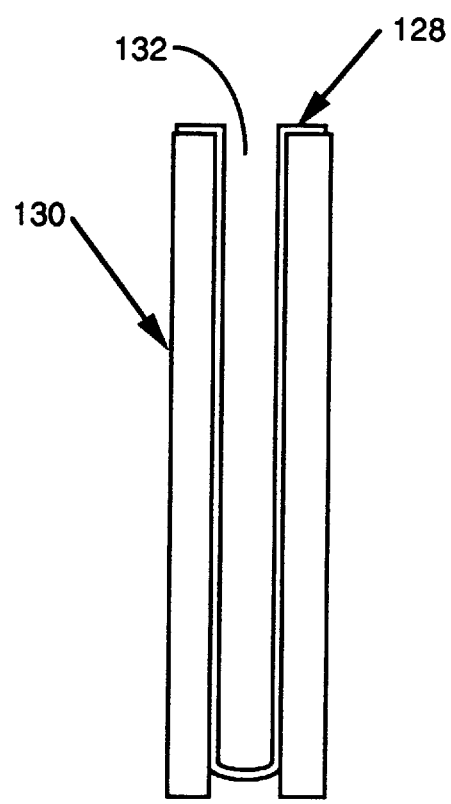

As shown in FIGS. 12a and 12b, the present invention also describes an extraction device 129. The extraction device 129 comprises an insert 128 for containing a sample during supercritical fluid extraction. The insert 128 is retained within a container 130 having a chamber 132. Preferably, the insert 128 is porous and can be comprised of teflon material such as PTFE. The insert 128 described herein has advantages over the prior art in a number of ways: 1) it allows the user the convenience of filling an inexpensive disposable vessel outside the laboratory or at a field or plant site and then easily transport it to the laboratory, and 2) it improves a quantitation by allowing for weight on a balance that is a small percent of the total weight of the vessel liner plus matrix, rather than a large percentage of the total weight as in the prior art.

In the operation of the insert 128, which is comprised of teflon, it is filled with a sample, such as soil, at a site. The insert 128 is brought back to the laboratory and is inserted into the chamber 132 of a stainless steel container 130 adapted to contain the liner 128. The container 16 with insert 128 is then connected to an SFE system 10 and the analyte from the sample is extracted. The liner 128 is porous and thus does not have to be punctured during extraction. The supercritical fluid flows through the microscopic holes in the teflon to the sample to extract analyte, from the sample. The holes are small enough to prevent passage of the sample matrix therethrough. Accordingly, the liner 128 acts as a filter. After extraction, the liner 128 with the extracted sample is disposed of.

Figure 11:
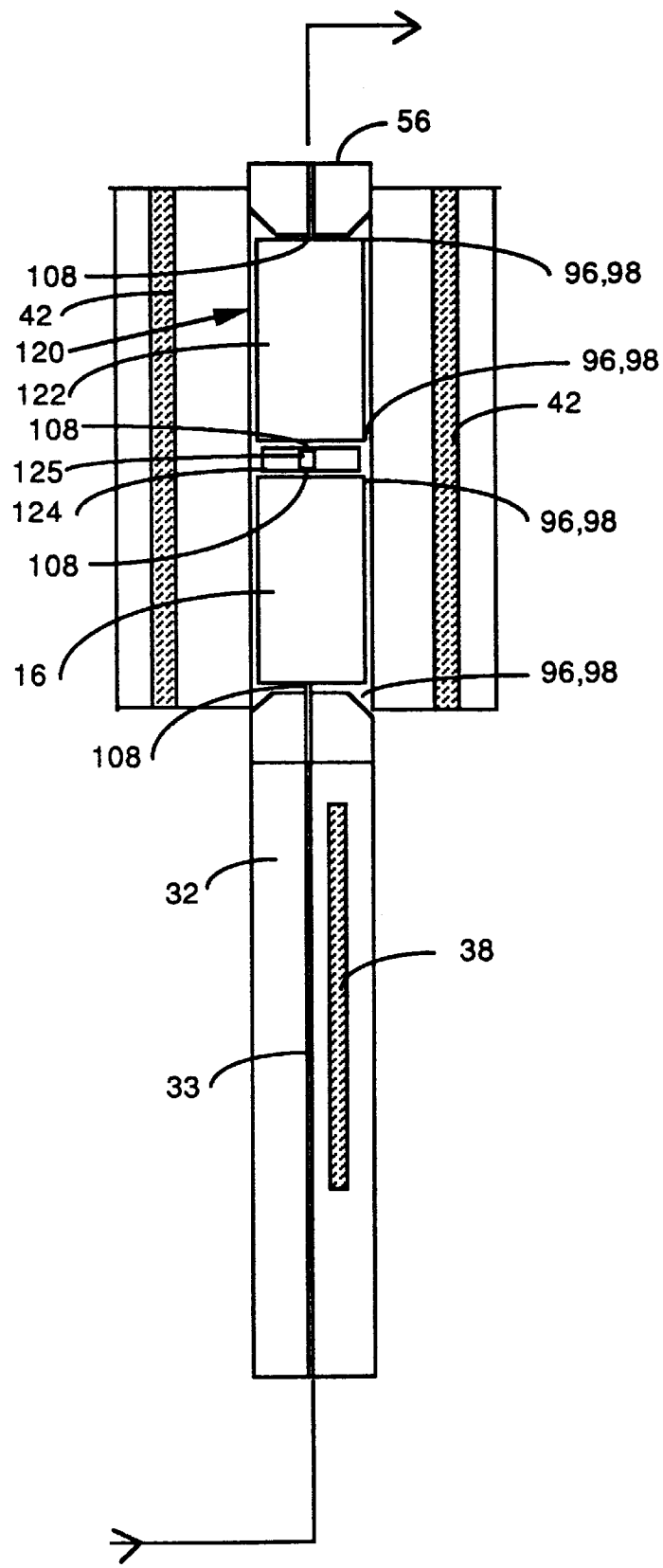
FIG. 11 is a schematic representation showing a second vessel for removing water installed after the extraction vessel.

As shown in FIG. 11, the SFE system 10 can include means 120 for removing water from the supercritical fluid with analyte. Especially in the environmental analysis area, many samples that must be prepared have a water content which can be anywhere from 1 to 70 percent by weight. Although water has a small solubility in supercritical fluid carbon dioxide, (~1.6% by weight), the flow of supercritical fluid entrains water in it and thus carries a much larger percentage of the water out of the matrix than would occur if solubility were the only factor. Thus, this water must be dealt with or it could plug the downstream plumbing and the restrictor 22. One method to prevent this plugging is by mixing an absorbent such as sodium or magnesium sulfate or hydromatrix (a form of diatomaceous earth) with the sample to absorb the water and prevent it from being carried from the vessel.

In another method and as specifically shown in FIG. 11, a second vessel 122 filled with an absorbent such as sodium sulfate, magnesium sulfate or hydromatrix is installed immediately after the extraction vessel 16. Preferably, an adapter 124 is used so that the seals of the two vessels can mate and be leak-free at high pressure. The adapter 124 preferably has two nipples 108 which open the seals of the extraction vessel 16 and the second vessel 122. A passage 125 in the adapter fluidically connect the two vessels 16, 122.

During SFE extraction, the supercritical fluid passes through the first vessel 16 with the sample matrix and entrains the water and solubilizes the analytes of interest and carries them into the second vessel 122. In the second vessel 122, the absorbent absorbs the water while the analytes are carried through the second vessel 122 in the supercritical fluid. In this manner, the water is removed from the SFE system 10. The outlet of the second vessel 122 then is connected to the downstream plumbing and the collection means 20.

As shown in FIG. 1, the SFE system 10 preferably also includes means 60 for providing a modifier to the supercritical fluid. The modifier providing means 60 is in fluidic communication with the supercritical fluid providing means 12, such as through a mixing tee 62. The modifiers are typically a liquid organic solvent such as methanol, ethanol, propylene carbonate, acetone, tetrahydrofuran, fomic acid, etc. that are blended with the carbon dioxide in 1 to 50% by volume or mole percent to form a mixture that retains much of the diffusion characteristics of the pure carbon dioxide phase but which has a much higher polarity and thus is able to solubilize polar analytes and extract the polar analytes from the sample matrix. The modifier providing means 60 can include a plurality of modifier pumps 127 for providing a plurality of different modifiers to the mixing tee 62. In this manner, a modifier mixture of the appropriate polarity can be added to the supercritical fluid to provide the specific polarity necessary during the extraction of each extraction vessel 16. Further, explanation on the use of modifiers can be found in S. H. Page, S. R. Sumpter, M. L. Lee, "Fluid Phase Equilibria in Supercritical Fluid Chromatography with $CO_2$-Based Mixed Mobile Phases: A Review", J. Microcol. September 4, 91–122, incorporated by reference. The modifier pump 127 introduces the modifier at a predetermined rate and pressure into the mixing tee 62 such that it mixes with the supercritical fluid without impeding its flow. Computer 64 controls the modifier pump 127.

The computer 64 automatically controls the functions of the SFE system 10. The computer 64 is programmed with the specific parameters for controlling the fluid extraction system 10, during each of the sample runs. These parameters can include, for instance, sample order, extraction temperature, supercritical fluid pressure, flowrate, modifiers content, flushing fluid content, static or dynamic extraction selection, valve timing and leak and plug detection, collection temperature, trap desorb temperature, desorbing fluid and flowrate, and fraction collection vial number. In this manner, the computer 64 can automatically control the fluid extraction system 10 to sequentially extract and collect analytes from a multitude of samples. The user can simply load the carousel 28 with samples, program the computer 64 with the necessary control information and collect the extracted analyte, each within their own vial, from a fraction collector carousel 66.

Preferably, the SFE system 10 includes means, such as the computer 64, for controlling the flow of fluid from the providing means 12 to the extraction vessel 16 and to the collecting means 20 such that any leaks or plugs are detected. For instance, as will be described in greater detail below, the computer 64 follows an algorithm which sequentially controls the valves of the SFE system and monitors the pump during each stage. By comparing the action of the pump with predetermined standards, leaks and plugs in the SFE system 10 can be identified and quantified before, during and after each sample run.

Since the SFE system 10 operates at pressures up to 680 atmospheres (atm) and with a fluid with a relatively high diffusion coefficient ($10^{-3}$ to $10^{-4}$ gm cm$^{-1}$ sec$^{-1}$), plumbing leaks in the SFE system 10 due to either loose fittings or leaking check valves happen with some regularity. In the prior art, quantification of these leaks have been ignored since they are very difficult to calculate and measure. Yet flow leaks have a detrimental effect on extraction results. In SFE, it is important to measure the number of milliliters of fluid or grams of fluid that actually pass through an extraction vessel 16. By knowing the amount of fluid passing through the extraction vessel 16 as well as other extraction parameters such as pressure and temperature, one can develop an extraction procedure that can then be replicated in other laboratories with other SFE instruments.

Leaks in an SFE system 10 can occur with every extraction, (e.g., extraction vessels are changed, loosened and tightened with every extraction and pump check valves can leak). Leak rates can change with different system pressures (i.e. the higher the pressure, the greater the leak). Thus, there is a unique leak rate that occurs with every extraction. If the fluid leak is not quantified, then the amount of fluid passing through the vessel 16 has an error in it (the leak rate) and thus will cause poorer laboratory to laboratory and instrument to instrument reproducibility that would occur if the leak rate was known and quantifiable. In addition, if the leak rate is too large, then the extraction will not occur at all as most of the fluid goes out the leak and little through the extraction vessel 16. Thus, overall, it is desirable to be able to identify, quantify and report to the user the system leak rate for every extraction.

Another problem with SFE systems is the plugging of plumbing, valves, frits or filters downstream of the extraction vessel 16 with agglomeration of analytes. It is well known that certain analytes, especially ones at high concentration levels can agglomerate together and form larger particles. These larger particles can then plug the SFE system 10. Using the same flow algorithms used to determine fluid flow and fluid leaks, the SFE system 10 can determine if there is a plug or no flow or low flow conditions in the instrument and then report this condition to the user.

The supercritical fluid pump 126 is capable of measuring the flow of liquid through its pump heads. As shown in FIG. 1, the first step of the leak detection method closes valves V5 and V3. This effectively isolates the pump 126 from the rest of the extraction system 10. The pump 126 is set to deliver a constant pressure equal to the desired extraction pressure. After a suitable delay to allow the pump heads and the associated plumbing to reach thermal equilibrium with the environment, a flow reading is taken. This flow is due to leaks in the pump 126. This flowrate is called the pump leak rate. Once an accurate pump leak rate is established, valve V3 is opened and valves V1, V6 and V7 are closed. This exposes the extraction vessel 16 to the supercritical fluid delivered from the pump 126. Since all the exit valves from the extraction vessel 16 are closed, any additional flow must be attributed to leaks from the extraction vessel 16 and its associated plumbing. By waiting an appropriate time for the pump 126 and extraction vessel 16 to reach thermal equilibrium with their respective environments, the resulting flow is the sum of the pump leak rate and leaks within the extraction vessel plumbing. By taking a flow reading of the combined system and subtracting the pump leak rate, the leak rate of the extraction vessel 16 is calculated. This is called the extraction vessel leak rate. The final stage of the leak and plug detection method is to open valve V1 to allow the combination of supercritical fluid and dissolved analyte to pass to the restrictor 22. It is the total flow through the restrictor 22 which is desirable to know since this determines the amount of analyte carried out of the extraction vessel 16 to be collected in the collection means 20. Once the pump leak rate and the extraction vessel leak rate are known, these values may be subtracted from the total flowrate as seen by the pump 126 during the final stage with V1 open. The resulting flowrate is the total flow through the restrictor 22. Thus, leaks may be both detected in a static extraction environment (i.e. V1 closed) and corrected for in a dynamic extraction environment (i.e. V1 open).

It is possible to also measure the flow of fluid through a supercritical fluid extraction system 10 by measuring the flowrate of gas that is expelled from the system past the restrictor 22. In order to collect the desired analyte, the supercritical fluid is allowed to expand to its normal volume at atmospheric pressure. Since there is a known density ratio between the supercritical fluid state and the expanded gas state the supercritical flowrate may be calculated from the expanded gas flowrate. By measuring the expanded gas flowrate with an expanded gas flow meter 172, as shown in FIG. 1, and performing the appropriate calculation the flowrate of the supercritical fluid exiting from the restrictor 22 can be determined. The entire system leak rate can be computed by subtracting the liquid flowrate at the restrictor 22 from the liquid flowrate out of the pump 126. This determination can be made even if the leak rate changes while the extraction system is continuously flowing. In addition, the resulting leak determination is more accurate because it includes all of the valving and the restrictor 22 in the flow path. After leaks and plugs are tested, valve V1 is opened to allow supercritical fluid with analyte to flow to the restrictor 22.

Figure 8A:
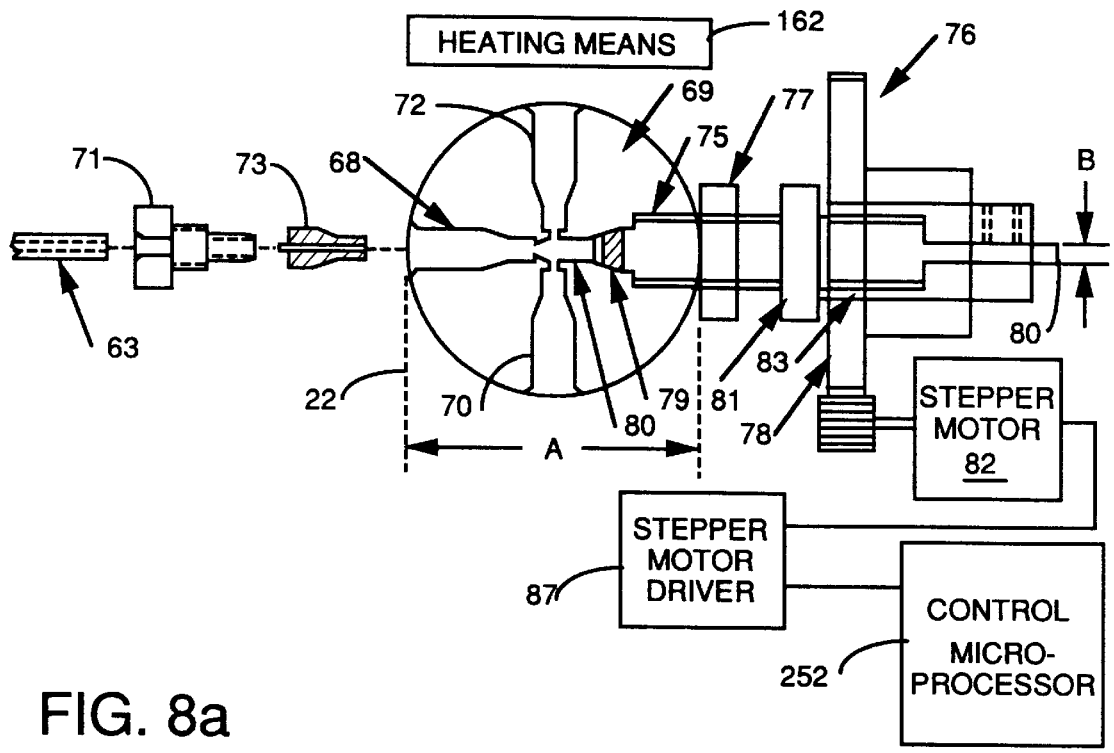
FIGS. 8a–8e are schematic representations showing the restrictor of the present invention.
Figure 8B:
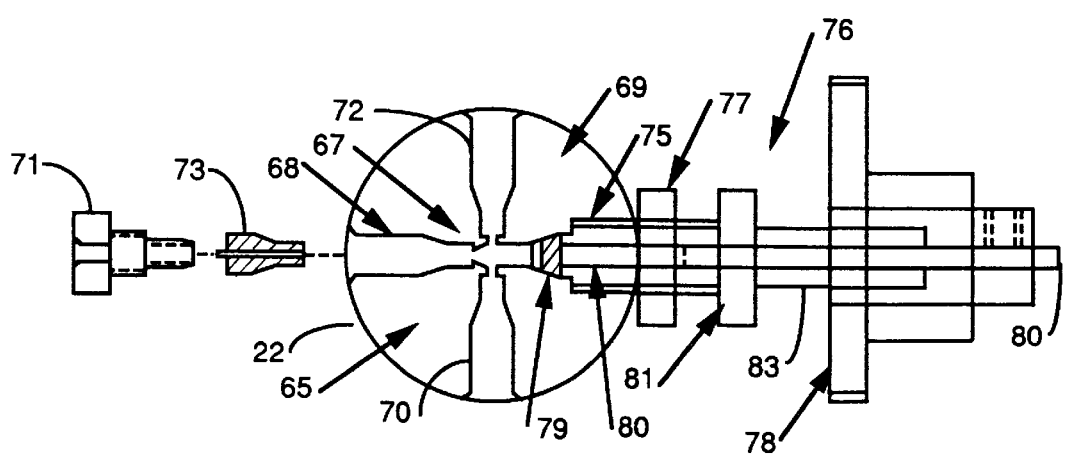

There is a need in SFE to reduce the pressure of the supercritical fluid after it exits the extraction vessel from its high pressure (up to 680 atm) down to atmospheric pressure so that the analytes can be effectively collected. Restrictor 22 does this automatically. Referring to FIGS. 8a and 8b, there is shown the restrictor 22. Preferably, the restrictor 22 is automatically controlled by the control microprocessor 252 and the computer 64. The restrictor 22 has a channel 65 which is preferably comprised of a first port 68 in fluidic communication with the extraction vessel 16, a second port 70 in fluidic communication with the collecting means 20 and a third port 72 in fluidic communication with means 74 for providing desorbing solvent to the collection means 20. A portion 67 of the channel 65 has a variable inner diameter.

In a preferred embodiment of the restrictor, the portion 67 of the channel 65 with the variable inner diameter is a needle member 80 adjustably projects into the first port 68 to restrict the flow of fluid with analyte therethrough. The first, second and third ports 68, 70 and 72 are threaded openings in a housing 69. The supercritical fluid with analyte is provided to the first port 68 through stainless steel tubing 63. Preferably, the tubing 63 has a ¹⁄₁₆" OD and a 0.030" ID. The tubing is connected to an adapter 71, which is threaded into the first port 68 and sealed against seat member 73. Across from the first port 68 in the housing 69 is a fourth threaded port 75. A needle member 80 is threaded into the fourth port 75. The needle member 80 comprises a valve nut 81 which threads into the fourth port 75 and a first nut 77 having an opening which is threaded onto valve nut 81 to secure the needle member 80 into the fourth port 75. The valve nut 81 secures a ferrule 79 having an opening in the fourth port 75, to seal the fourth port 75. A needle member 80 projects through the opening of the first nut 77, valve nut 81 and the seal 79. A gear 78 is threaded onto a threaded extension 83. The gear is fixedly attached to the needle member 80 by a set screw in threaded extension 83. Threaded extension 83 is then threaded onto value nut 81. By turning the gear 78 on the threaded extension 83, the needle member 80 can be adjusted relative to the first port 68 and the seat member 73 contained within first port 68 to adjust the inner diameter of the channel 65. The threading of the threaded extension 83 and the gear is extremely fine to allow for precise adjustment of the needle member 80. A motor 82 is used to turn the gear 78 on the threaded extension 83. The computer 64 controls the motor 82 based on desired flow of fluid through the control microprocessor 252 and the stepper motor driver 87.

Referring to FIG. 8a and FIG. 14a, the control of restrictor 22 is accomplished by the user setting a desired flowrate in computer 64. Computer 64 downloads to the control microprocessor 252 this desired flowrate. Control microprocessor 252 then calculates an actual flowrate of the pump (as described previously) and compares the desired or set flowrate to the actual flowrate. Control microprocessor 252 then calculates if any corrective changes must occur in restrictor 22 by its control algorithms. If the actual flowrate does not match the set flowrate, then control microprocessor 252 sends to stepper motor driver 87 the number of motor pulses of change that should occur. The stepper motor driver 87 then controls stepper motor 82 to move that number of pulses. The motor moves the needle member 80 in restrictor 22 and a new flowrate is created. Then, the control microprocessor 252 calculates the new actual flowrate (as described previously) and the control cycle continues.

If control microprocessor 252 calculates that actual flow is less than set point flow, then it will control needle member 80 to move away from the seat member 73 and thus open up the restrictor. If control microprocessor 252 calculates that actual flow is greater than set point flow, then it will control needle member 80 to move toward seat member 73 and thus close the restrictor. FIG. 8a shows the needle member 80 fully projecting into the first port 68. FIG. 8b shows the needle member 80 retracted from the first port to allow, for instance, the desorbing solvent from the third port 72 to freely flow to the second port 70, although it is not necessary to retract the needle member 80 from the first port to allow desorbing solvent to flow, since there is adequate clearance around the needle member 80 for the desorbing solvent to flow.

Figure 8C:
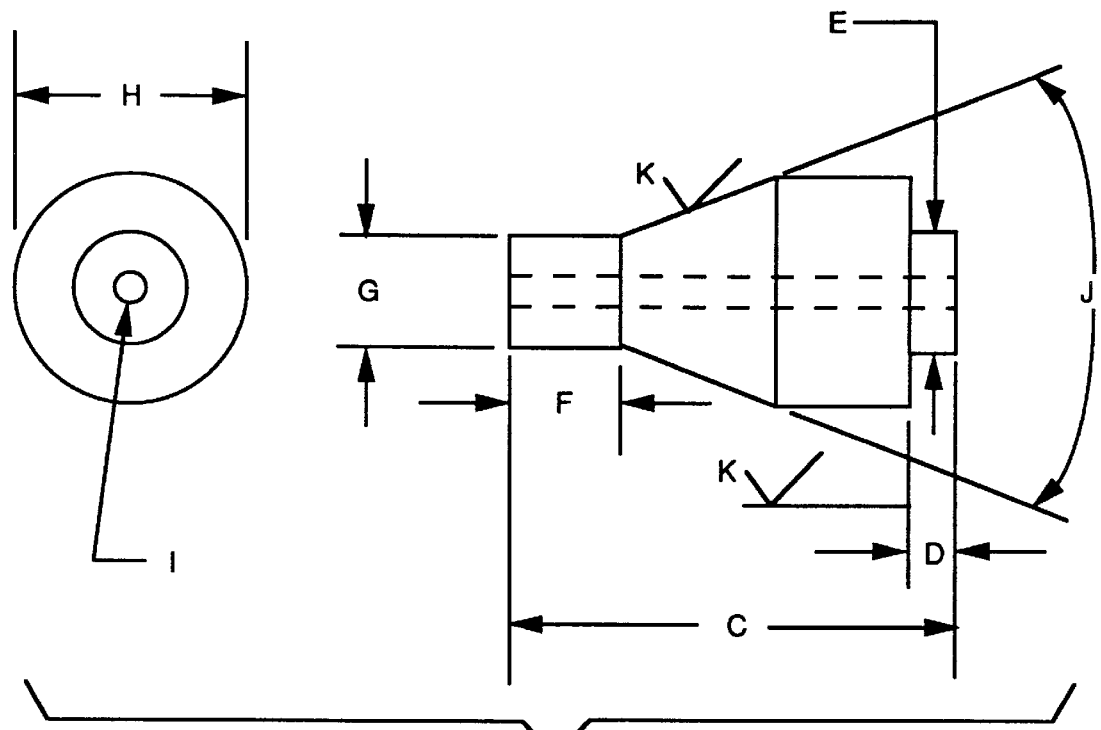
Figure 8D:
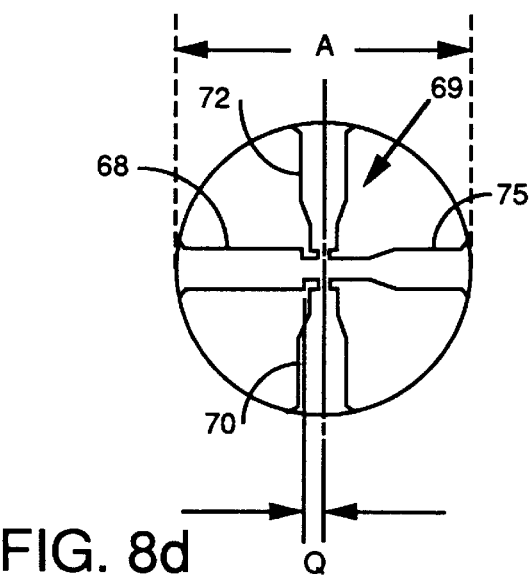
Figure 8E:
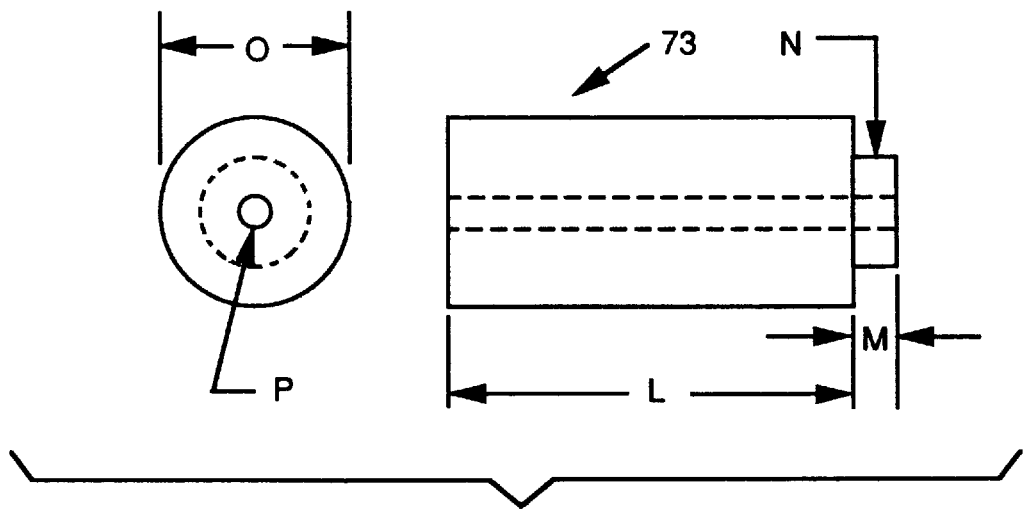
Figure 9A:
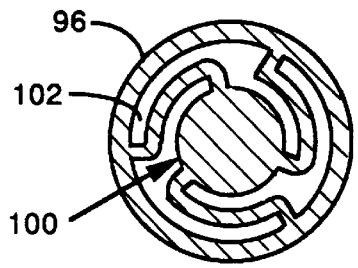
FIGS. 9a–9d are schematic representations showing an extraction vessel having check valves.
Figure 9B:
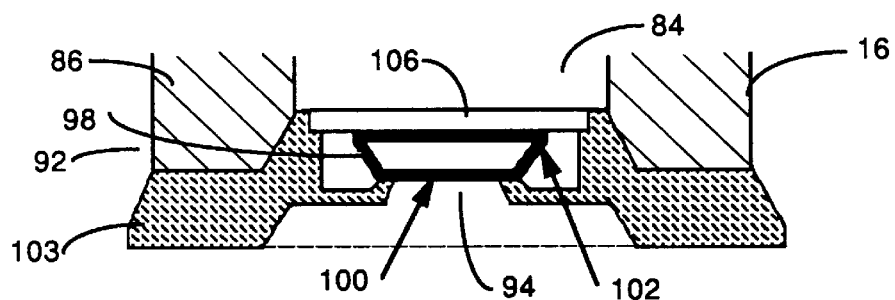
Figure 9C:
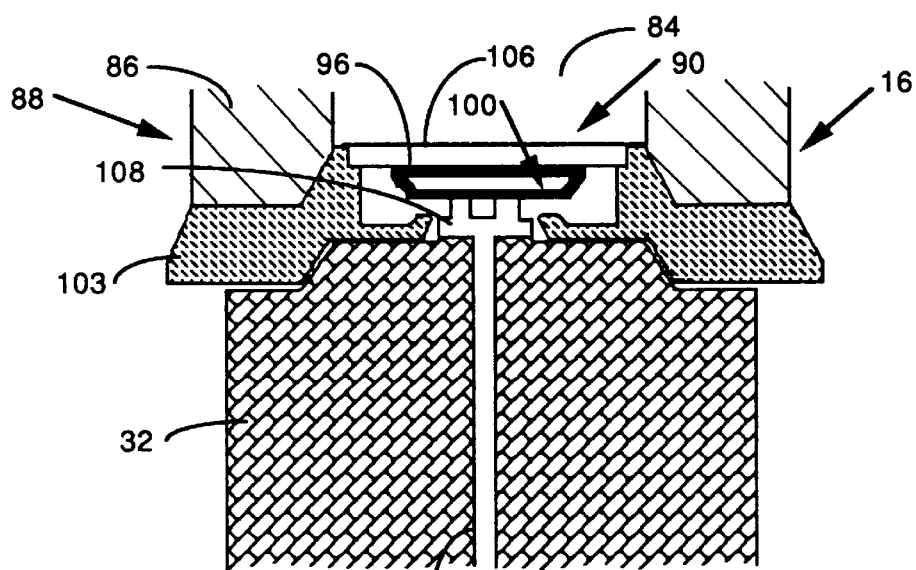
Figure 9D:
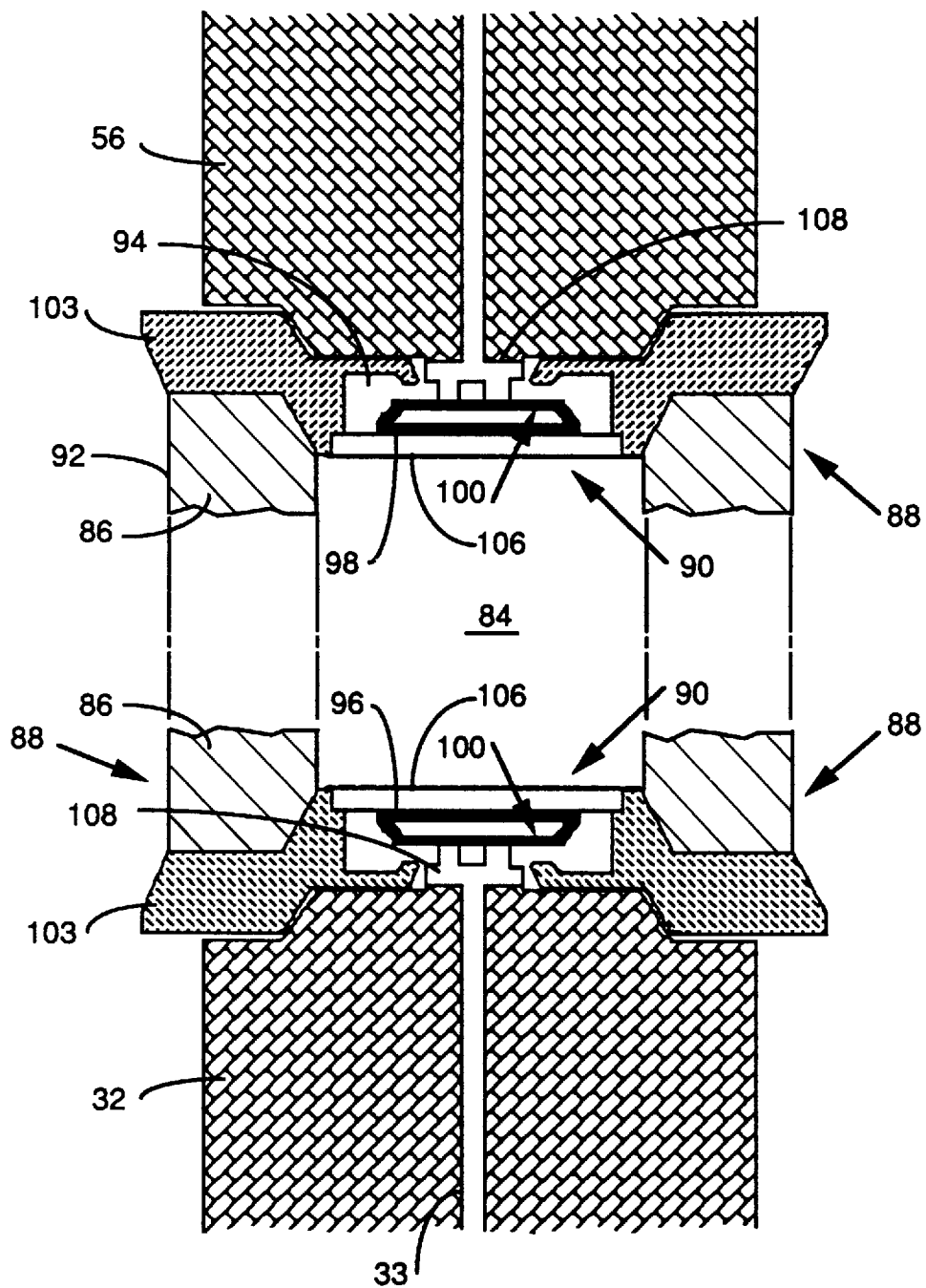
Figure 10A:
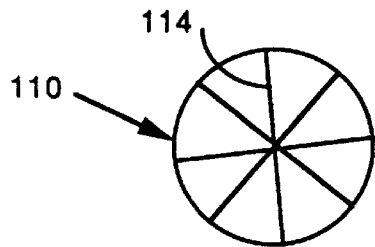
FIGS. 10a–10d are schematic representations showing the extraction vessel having sealing membranes.
Figure 10B:
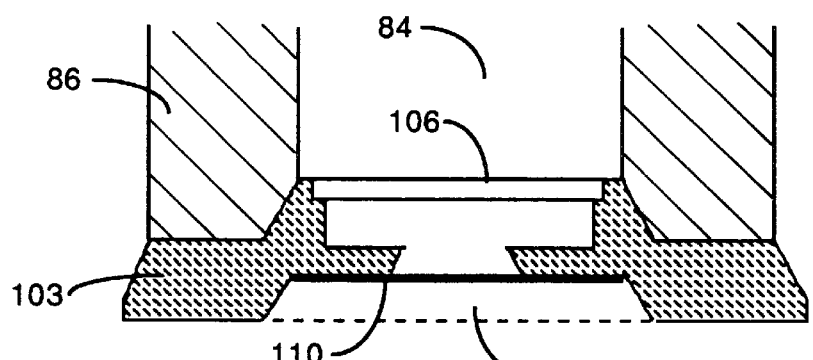
Figure 10C:
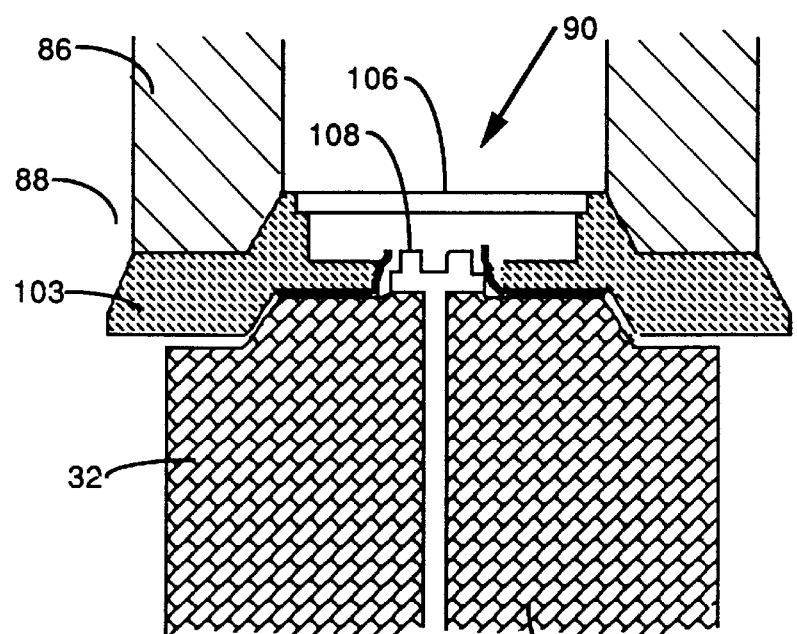
Figure 10D:
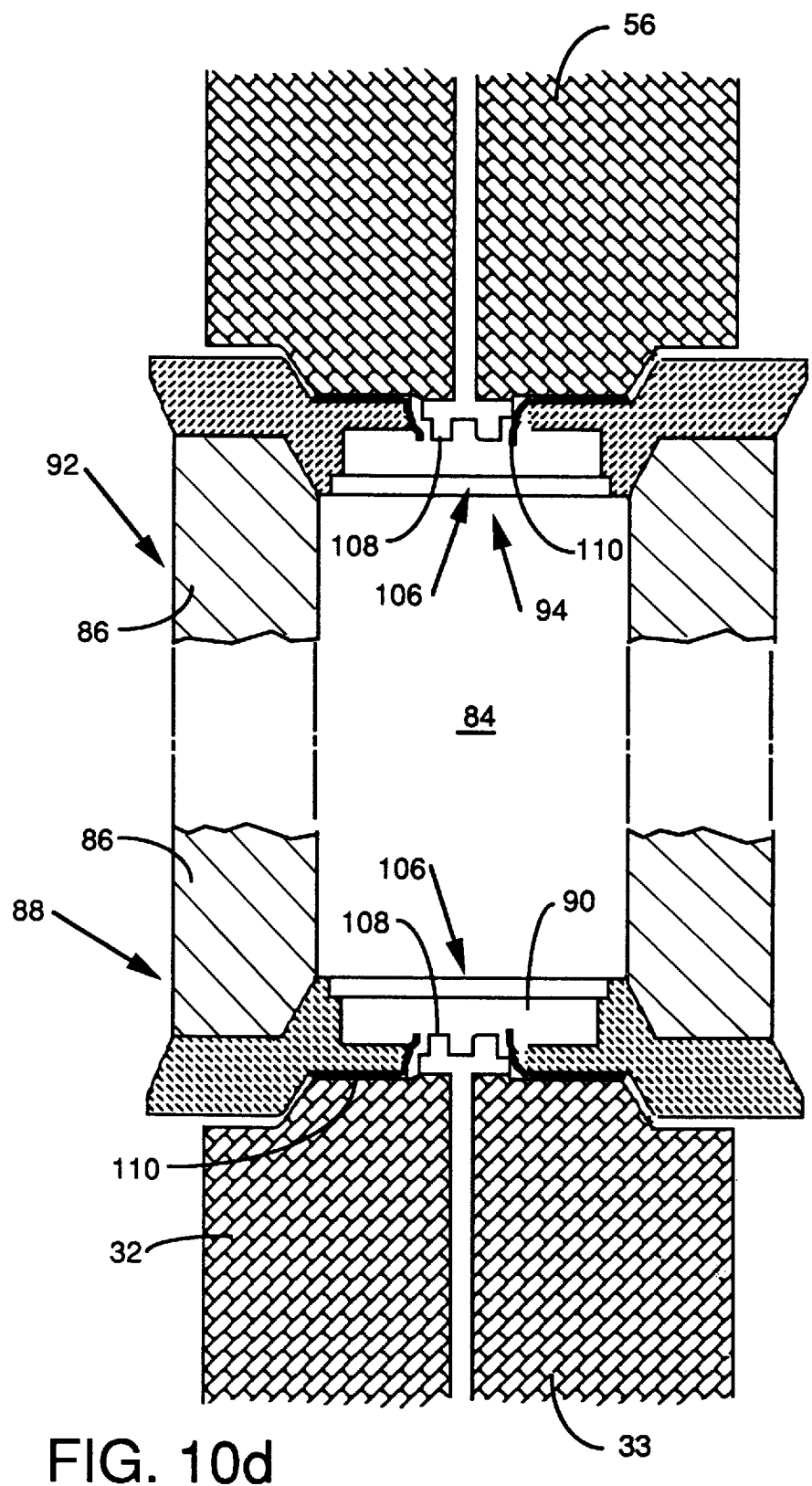

FIG. 8c shows a seat member 73 having an angular profile for mating with the similarly shaped angular profile of the first port 68 of the housing 69, as shown in FIGS. 8a and 8b. Alternatively, the first port 68 of the housing 69 can have a shape as shown in FIG. 8d. The seat member 73 for fitting into the shape of the first port 68 as shown in FIG. 8d is shown in FIG. 8e. The following represents the dimensions as represented by reference characters A–Q in FIGS. 8a–8e.

| | | |
|---|---|---|
| A = 1" | G = .062" | M = 0.28" |
| B = ¹⁄₁₆" | H = .14" | N = .060" |
| C = .29" | I = .015" ID | O = .140" |
| D = .028" | J = 40° | P = .0156 ID |

-continued

| | | |
|---|---|---|
| E = .06" | K = 32 finish | Q = .050" |
| F = .07" | L = .290" | |

It should be noted that the restrictor 22 has very small dimensions as compared to previous SFE restrictors. For instance, the total assembled length and width of the restrictor 22 is less than 2.5 inches and 1.5 inches, respectively. In this manner, reliable and precise control of supercritical fluid restrictor can be accomplished with a restrictor which is extremely small, and thus has extremely small dead volume. Small dead volume is important because the smaller the dead volume, the less likely that the restrictor will plug with analytes because the analytes do not have a volume to collect in or lodge in and thus start to form a plug. The small dead volume also reduces cross-contamination because analytes from a previous extraction do not have a place to collect and thus contaminate the extraction of analytes from a subsequent extraction. The restrictor 22 preferably has a minimum dead volume of 0.31 microliters, a maximum dead volume of 0.86 microliters and a nominal dead volume of 0.50 microliters.

Restrictor 22 also has the following additional advantages. The variable restrictor has the ability to accurately control carbon dioxide flows preferably in the 0.3 to 7.0 ml/min. range due to its very small dimensions and the control algorithms previously discussed.

Restrictor 22 has the ability to keep the depressurized carbon dioxide from freezing in the outlet of the valve, due to the heating means 162 (see FIG. 8a or FIG. 1). The heating means 162 consists of a cartridge heater and an RTD. The cartridge heater is connected to a power source controlled by control microprocessor 252 and the RTD is connected through a relay also to control microprocessor 252. Control microprocessor 252 then reads the RTD and compares that actual reading to the set temperature, as set by the user on computer 64, and then controls the power supply and thus the cartridge heater so that heating means 162 reaches the set temperature. Heating means 162 heats housing 69 which in turn heats the fluid flow entering first port 68, such that the expanded gas exiting second port 70 does not freeze. Supercritical fluid carbon dioxide upon depressurization, expands rapidly and cools due to Joule-Thompson effects. Carbon dioxide freezes into a solid at temperatures less than minus 65° C. Heating means 162, which is controlled at temperatures typically between 50° C. to 100° C. is powerful enough to overcome the Joule-Thompson effect so that the fluid exiting second port 70 is in the temperature range of −50° C. to +30° C. and preferably 25° C.

Restrictor 22 also has advantages over previous restrictor devices in that it has a ferrule 79 to seal the needle member 80 into the fourth port 75. The ferrule 79 has smaller dead volume than spring loaded seal with a larger dead volume. The smaller dead volume has advantages as described previously. Restrictor 22 also is constructed of stainless steel with poly-ether-ether-ketone (PEEK) seals. This has advantages over previous designs such as disclosed in U.S. patent application Ser. No. 07/848,424, incorporated by reference, because of increased durability, lack of fatigue of PEEK tubing parts, and smaller mechanical forces to automate which require smaller motors and less expensive cost.

Restrictor 22 also provides more precise control due to the PEEK seat member 73. Since the seat is made of PEEK instead of the more typical stainless steel or specialty steel, the seat member 73 is more pliable. Thus, seat member 73 flexes under the load of needle member 80 and this allows for more precise control of the restrictor. Thus, restrictor 22 can more precisely obtain a set flowrate than previous restrictors. Even though the seat member 73 is pliable, it cannot be too pliable or the seat will yield and thus fail after some time. This seat member 73 made from PEEK is durable enough to last for an extended amount of time, yet pliable enough to allow more precise control.

Restrictor 22 also employs stepper motor 82 to drive the needle member 80. The use of a stepper motor 82 allows for more precise control because the turning of the stepper motor can be precisely controlled via stepper motor driver 87 and control microprocessor 252.

Another advantage of restrictor 22 is the ability to totally flush the restrictor with a flush liquid which is the same liquid used as the desorbing solvent dispensed by pump 170. Since the third port 72 exists and is plumbed to pump 170, pump 170 can dispense a liquid solvent such as methanol, methylene chloride, or other common liquid solvent that flows into the third port 72 and exits from the second port 70. This desorbing or flush liquid then can wash the needle member 80, housing 69 and seat member 73 to clean out any residual analytes that could have deposited on the inner surfaces of restrictor 22. Since the desorbing means 74 is used for this restrictor flush and since desorbing means 74 is controlled from computer 64, the entire flushing of restrictor 22 can be automated and pre-set by the user.

Yet another advantage of restrictor 22 is that it is flow controlled versus pressure controlled. The parameters of pressure, temperature and fluid flowrate all effect the extraction efficiency of SFE. Pressure and temperature have the largest effects while flow the smallest effect. In the prior art, the systems typically operate with either a flow controlled pump combined with a variable pressure controlled restrictor or a pressure controlled pump with a fixed, nonvariable restrictor to control flow. System 10 incorporating restrictor 22, combines the pressure controlled pump with a variable flow controlled restrictor. This allows the fastest (in time) control response to be at the fluid providing means 12 which controls pressure, a more critical parameter to the extraction, and the slower (in time) control response for flow on the restrictor where it is less critical.

Another advantage of restrictor 22 is its ability to allow water to pass through the restrictor without plugging. The restrictors used in the prior art are very susceptible to plugging when water passes through the restrictor. Many types of environmental samples have a water content. Although there are methods to absorb the water during the extraction step, it is much easier to just let the water become both solubilized and entrained in the supercritical fluid flow exiting the extraction vessel and then to carry that water through the restrictor and into the collection means.

The problem in the prior art in doing this is that the water typically plugs the restrictor. Restrictor 22 does not have this problem. When water goes through the restrictor 22, the water causes the flow to slow down, the restrictor control system detects this and opens up the restrictor 22 to flow by moving the needle member 80 away from seat member 73. In this manner, restrictor 22 has been tested by filling an extraction vessel with 5 milliliters of water, pressurizing the vessel with 500 atm of carbon dioxide and then opening up valve V1 to allow the water to flow through restrictor 22. The plug of pure water being pushed through restrictor 22 by the $CO_2$ does not plug the restrictor 22.

Another advantage of restrictor 22 is its ability to allow high modifier concentrations to pass through the restrictor without plugging. The restrictors used in the prior art, especially restrictors made of fused silica, are very susceptible to plugging when any high level of modifier (greater than 10%) passes through the restrictor. Restrictor 22 operates smoothly according to the control algorithm when using modifier concentrations as great as 50%.

At the end of an extraction, the valve V1 switches so that the flow of supercritical fluid from the extraction vessel 16 is shut off from the collection means 20. The closing of valve V1 is done so that the collection means 20 can function in an isolated manner from the extraction chamber 18. This results in a state where the extraction vessel 16 is pressurized with fluid. The pressurized fluid must be vented from the extraction vessel 16 so that the extraction vessel 16 can reach atmospheric pressure and the extraction vessel 16 can subsequently be taken out of the extraction chamber assembly and returned to the carousel 28. Then, the next extraction vessel 16 from the carousel 28 is loaded into the extraction chamber assembly 18 to begin the next extraction.

Accordingly, the SFE system 10 preferably provides a vent valve V2 for venting supercritical fluid downstream from the extraction chamber 16. The vent valve V2 is located downstream of the extraction chamber 16. The vent valve V2 has a first path 116 and a second path 118. The collecting means 20 is in fluidic communication with the extraction vessel 16 through the first path 116. The supercritical fluid is vented from the extraction vessel along the second path 118 through a vent. Venting occurs by: 1) closing the valves V3, V6 and V7 between the supercritical fluid and modifier pumps and the extraction vessel 16 to cut off the source of the supercritical fluid and modifiers, 2) opening valve V1, and 3) switching V2 to vent the fluid in the extraction vessel 16. Preferably, vent valve V2 is a 4-port, 2-way switching valve. It should be noted that this venting of the fluid in the extraction vessel 16 could be done through the collection means 20. However, this is usually impractical because it takes too much time since the analyte must be first collected from the collection means with desorbing solvent before venting occurs. The downstream vent valve V2 allows venting and desorbing to occur simultaneously.

A downstream vent valve is superior over the prior art where either plumbing fittings have been broken to vent the system or an upstream vent valve has been used. The advantages of the downstream valve are: 1) if analytes are still contained in the sample matrix, then the downstream plumbing lines are probably contaminated with analytes also. By venting downstream of the extraction vessel 16, one is flushing through these contaminated lines and cleaning them. When using an upstream vent of the extraction vessel, one is contaminating the upstream plumbing lines that were previously "clean" of analytes; and 2) the opening and closing of a valve V2 can be automated and thus opened and closed automatically by the computer 64 of the SFE system 10 versus the user loosening a fitting connection, which is labor intensive and not readily automatable.

With respect to flushing of the extraction system 10, it is very typical that there are incomplete extractions during the development of an SFE method or procedure, i.e, analytes are still remaining in the extraction vessel 16 and in the downstream plumbing from the extraction vessel 16 to the collection means 20. Accordingly, it is desirable to have a mechanism to be able to flush out the remaining analytes so that the system is "clean" for the next sample extraction.

This SFE system 10 flushing is accomplished by using a blank (i.e. empty) extraction vessel 16 in the carousel 28. The SFE system 10 loads this blank vessel from the carousel 28 into the extraction chamber assembly 18, as shown in FIG. 2. The system 10 can then be programmed to deliver from the pumping system either 100% supercritical fluid, 100% modifier or a programmed combination of the two (supercritical fluid/modifier mixture) through the plumbing of the SFE system 10 so that the polarity of the fluid used to clean the system can be matched with the polarity of the analytes that contaminate the system 10.

The flushing fluid is delivered from the pumps 126 and 127, through the inlet tubing to the blank vessel and through the downstream plumbing to the 4-port, 2-way switching valve V2. This valve V2 can be switched so that the flush can either be directed into the collection means 20 to also clean it of remaining analytes or to the vent to allow escape of the flushing fluid.

In the preferred embodiment, the collecting means 20 includes a collection trap 164 which can be comprised of carbon steel, stainless steel and PEEK or teflon and is either directly connected or attached or is connected with stainless steel tubing to the restrictor 22. During collection, the collection trap 164 is cryogenically cooled with trap cooling means 174, such as with liquid $CO_2$. The cooling liquid $CO_2$ is provided by known technique about the collection trap 164 and includes an on/off valve to deliver $CO_2$ which can be controlled by the computer 64.

Desorbing fluid of the collecting means 20 is provided to the collection trap 164 with a desorbing pump 170 through valve Vll which can be controlled by the computer 64 where it solubilizes the analyte in the trap and carries it out of the trap. During desorbing, the collection trap 164 is heated with heating means 168 such as an inductive heating coil 168 to facilitate desorption of the analyte by the desorbing fluid. The analyte dissolved in the desorbing fluid flows preferably to a selected collection vial held with the fraction collector carousel 66. More detailed information about the collecting means 20 can be found in U.S. patent application Ser. No. 07/662,255, by Ashraf-Khorassani now U.S. Pat. No. 5,205, 987 et al., which is incorporated by reference.

Figure 15A:
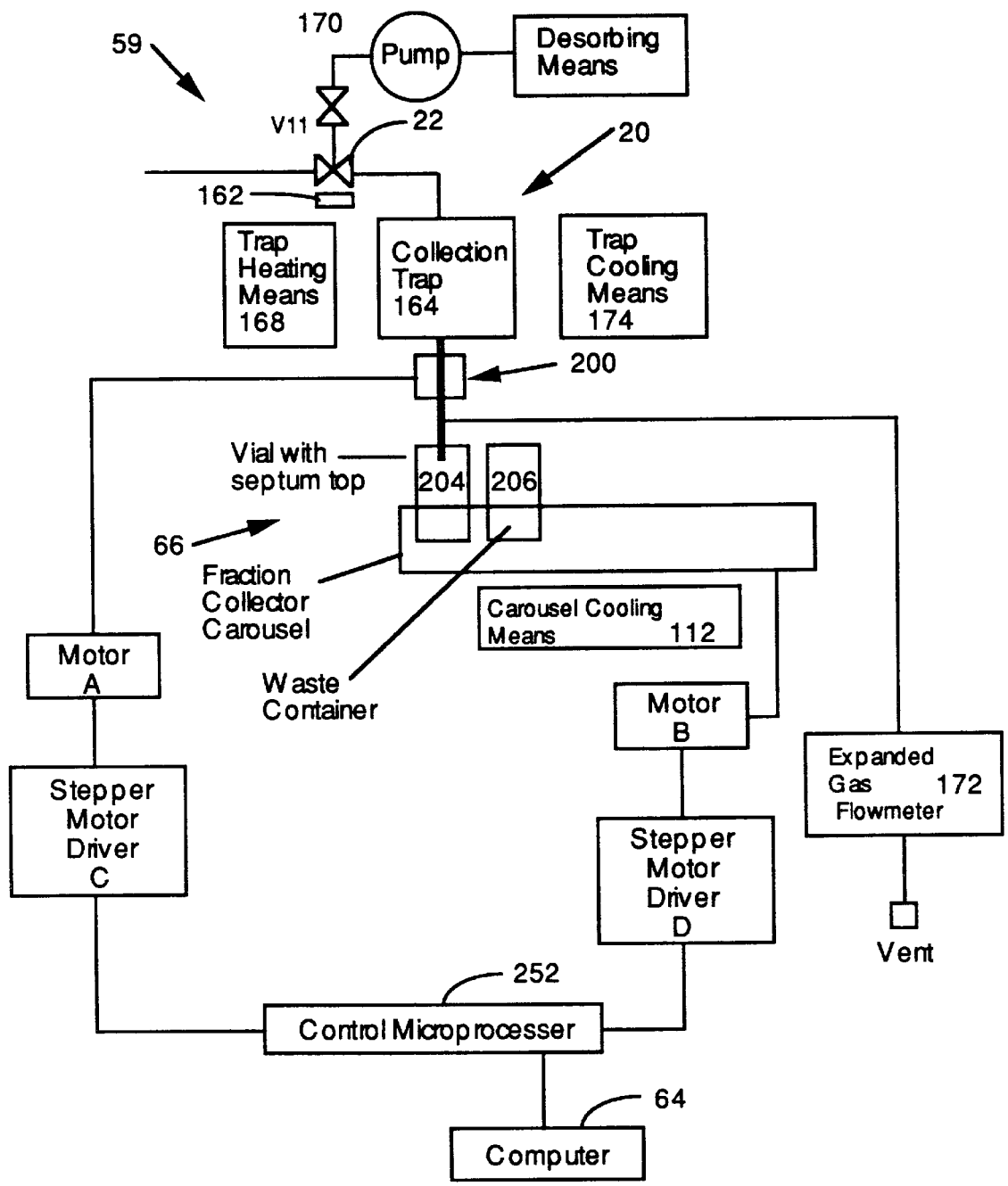
FIG. 15a is a schematic representation of a fraction collector system.
Figure 15B:
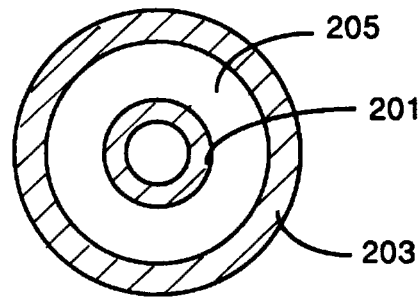
FIG. 15b is a schematic representation of an axial bottom view of a greater needle.
Figure 15C:
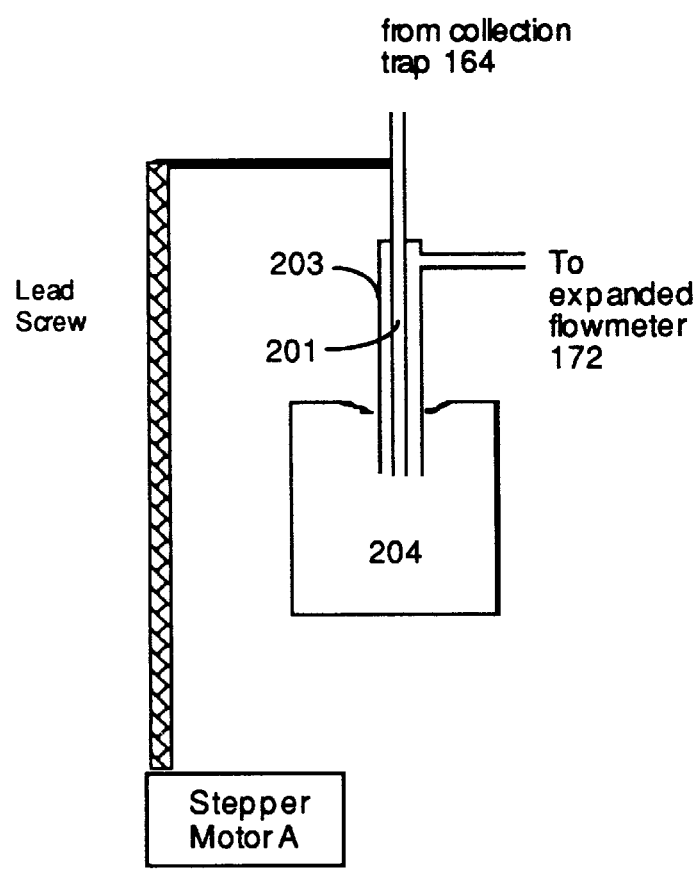
FIG. 15c is a schematic representation of a needle assembly.

The fraction collecting system 59, as shown in FIGS. 15a, 15b and 15c, is comprised of the following. The $CO_2$ exiting the collection trap 164 (when extracting) or the desorbing fluid with analytes exiting the collection trap 164 (when desorbing) flow through a needle assembly 200. The needle assembly 200 consists of a greater needle having an input and an output which is preferably a 2-part needle that has an inner needle 201, an outer needle 203, and an annular area 205 between the outside surface of the inner needle 201 and the inner surface of the outer needle 203. Thus, fluid flow can occur through either the inside of the inner needle 201 or through the annular area 203. The needle assembly 200 also consists of a clamp that holds the greater needle. The clamp with the greater needle is driven by driving means, such as a stepper motor that can drive the clamp and the greater needle in either an upward or downward motion.

The fluid exiting the collection trap 164 flows through the inner needle to a collection vial 204, which is a glass vial with a teflon or rubber septum. The septum is secured to the vial 204 with a threaded cap. The vials 204 can be either a 2, 6 or 12 ml vial and are typically made of glass.

The greater needle pierces the septum by the clamp traveling downward until the greater needle pierces the septum. Then the fluid flow through the inner needle 201 can occur such that either the $CO_2$ or the desorbing fluid with analytes can flow into the vial. The $CO_2$ or desorbing fluid with analytes at this point are preferably at nearly 1 atm pressure. The vial and septum form a closed system, such that when CO₂ is flowing into the vial, it will very quickly start to flow out the vial again by way of the annular area 205 of the greater needle. The CO₂ flow from the annular area is directed through a hole at the top of the annular area of the greater needle into a teflon line of ⅛ inch OD. The teflon line is connected to the expanded gas flow meter 172, which in turn is plumbed to a vent. When the desorbing fluid with analytes flow into the vial 204, it fills the vial 204 and thus one then has the collection vial with analytes in the desorbing fluid. It typically takes 2 ml of desorbing fluid to desorb the collection trap 164. The small amount air or CO₂ that was in the vial before desorbing began is forced out of the vial during desorbing through the annular area of the needle and into the teflon tube.

The collection vial is held in the fraction collector carousel 66. The carousel 66 can hold N vials, where N≧2 and is an integer and preferably either 48 of the 2 ml vials or 24 of the 6 or 12 ml vials. The needle assembly 200 and the fraction collector are driven by stepper motors A and B respectively. These stepper motors are electrically connected to stepper motor drivers C and D respectively. Both the stepper motor drivers are electrically connected to control microprocessor 252 which in turn is connected to computer 64. When computer 64 knows that an extraction is about to occur, it causes the needle assembly 200 to travel upward to disengage the needle from any vial by controlling it through the control microprocessor 252, stepper motor driver C and motor A. A stepper motor turns the fraction collector carousel to the next vial position as determined by the program. The needle assembly 200 then travels downward and the needle pierces the septum of the new vial. The extraction and desorption then occur as programmed.

The fraction collector carousel also contains a position where a waste vial 206 is located. The waste vial 206 may be a glass vial or preferably a 250 ml to 500 ml plastic container with a septum top. The computer 64 can program the waste vial to come into position under the needle assembly 200 so that the greater needle can pierce the septum of the waste vial. The waste vial is used when the user desires to program in a flush that needs a larger than 12 ml amount of solvent or in an extraction where there is a large amount of water in the sample and the user wants to direct the water to waste, while still collecting the analytes in the collection trap 164. The fraction collector carousel also has the carousel cooling means 112 in thermal communication with it and the vials, so that the vials can be cooled to as low as 4° C. as programmed by the user through computer 64.

The present invention is a method for supercritical fluid extraction. The method comprises the steps of moving an extraction vessel having a sample with an automated moving device into fluidic communication with a supercritical fluid extraction system so that the supercritical fluid can flow through the extraction vessel and extract analyte from the sample. Then, there is the step of extracting analyte from the sample with supercritical fluid. Preferably, after the step of extracting analyte, there is the step of collecting analyte from the fluid. Preferably, after the extracting and collecting steps, there is the step of analyzing the analyte with a liquid or gas chromatograph. Preferably, the extracting analyte step includes the step of extracting analyte from a sample with supercritical fluid under automated control by the supercritical fluid extraction device. Preferably, the moving step includes the step of moving the extraction from a first location to a second location in fluidic communication with the supercritical fluidic extraction device. Preferably, the moving step includes the step of selectively moving an extraction vessel with an automated moving device from a device for holding a plurality of extraction vessels into fluidic communication with a supercritical fluid extraction system.

The description of the preferred embodiment will be given using a typical extraction problem. The extraction of polyaromatic hydrocarbons (PAHs) in soil is an environmentally important problem. PAHs are difficult to extract due to their moderately polar chemical structure and their molecular weight. The sample extracted was a Solid Waste Laboratory Control Sample No. SRS103-100, Lot #AQ103 packaged by Resource Technology Corporation (RTC). This is a "native" or "real world" sample of PAHs in soil that was extensively analyzed by extracting with Soxhlet extraction and then analyzing the extracted analytes by gas chromatography (GC). The samples are packaged by RTC and sold as a known sample. This sample was extracted with supercritical fluid extraction.

The conditions of the SFE method are given in Table 1.

TABLE 1

SFE Optimization Parameters
PAHs in Soil
Sample:
Solid Waste Laboratory Control Sample SRS103-100, Lot# AQ103

| Extraction Conditions: | |
|---|---|
| Sample weight: | 275 to 340 milligrams (mg) for the 7 runs (see below) |
| Vessel size: | 0.5 ml |
| Extraction fluid: | |
| Primary fluid: | Carbon Dioxide |
| Modifier: | None |
| Pressure: | 450 atm |
| Temperature: | 65° C. |
| Flowrate: | 2.1 ml/min compressed (measured at 450 atm and 65° C.) |
| Extraction time: | |
| Static extraction time: | 5 min |
| Dynamic extraction time: | 30 min |
| Total extraction time: | 35 min |
| Total flow cumulative: | ~60 mls CO2 |
| Sample weight: | Run 1    290 mg |
|  | Run 2    335 mg |
|  | Run 3    330 mg |
|  | Run 4    310 mg |
|  | Run 5    340 mg |
|  | Run 6    300 mg |
|  | Run 7    275 mg |
| Analyte Collection Conditions | |
| Collection vial size: | 2.0 ml |
| Restrictor temperature: | 150° C. |
| Collection temperature: | −50° C. |
| Trap desorption temperature: | 30° C. |
| Desorbing solvent: | Methylene chloride |
| Desorbing solvent volume: | 1.0 ml |
| Desorbing solvent flowrate: | 0.5 ml/min |

In the operation of the preferred embodiment, to start an automatic extraction cycle of samples, 43 0.5 ml extraction vessels 16, each having a sample sealed within, and a blank 0.5 ml extraction vessel 16 are loaded into a carousel 28, as shown in FIGS. 1 and 2. The extraction vessel sizes are proportioned such that the longest and shortest extraction vessels 16 are both held securely by the carousel 28. In this case, all vessels are the same 0.5 ml size. Dimensions for the inside and outside diameters of the vessels 16 match standard ⅜" seamless pipe for the vessels' efficient coupling to the plunger 32 and end cap 56 so leakage is eliminated. The extraction vessels 16 are made of 316 stainless steel. Standard inside surface finish for the vessels 16 is about 50 microinches. Standard vessel sizes are 0.5 ml, 1, 3, 5 and 10 ml. The ends 88, 92 of each extraction vessel 16 have a seal member 103 with a spring biased check valve 96, 98 therein for sealing the inside of the extraction vessel 16 from the environment, as shown in FIGS. 9a–9d. A frit is positioned on each end of the extraction vessels. The frit 106 is made of sintered SS 316, 0.250 inches OD×0.040 inches and 2 micron porosity. The seal members 103 are comprised of PEEK plastic while the check valves 96, 98 are comprised of 316 stainless steel. The identity of each extraction vessel 16 as well as its respective vessel holder in the carousel 28 is noted as this information is needed to program the computer 64 of the extraction system 10 with the specific extraction parameters for each sample.

Referring to FIG. 2, the carousel 28 filled with extraction vessels 16 is loaded into the extraction system 10 by opening the enclosure 135 which contains the rotary table 30 and filling the carousel 28 such that each vessel 16, at the proper time can be introduced into the extraction chamber assembly 18. The rotary table 30 is mounted on a carriage 134 which supports the table. Though not specifically shown, a dowel pin and v-block are used to maintain alignment of the carousel 28 with the clamping mechanism 24 during operation. A clamp member 136, having a sensor, is used to secure the rotary table 30 and carriage 134 in an operational position.

The enclosure 135 is closed and a glycol/water cooling unit 29 within the enclosure is activated to maintain the extraction vessels 16 in a chilled environment which can be as low as 4° C. In this manner, thermal degradation and biological activity of the samples is arrested or prevented. Also cooling of the extraction vessels 16 decreases the vapor pressure of the analytes in the sample matrix, lowering the risk of leakage of analytes therefrom and thus supplementing the sealed features of the extraction vessels 16.

The clamping mechanism 24, as shown in FIG. 3, consists of a plunger 32, carriage assembly 138, two linear screws 140, c-frame 142, timing belts 144, pulleys 146, and motor with brake 148. The two linear screws 140, which are located on opposite sides of the plunger 32 are used to drive the plunger 32 against the extraction vessel 16 into the extraction chamber assembly 18 and to provide the necessary force to seal and maintain pressure within the extraction vessel 16 during supercritical fluid extraction. The plunger 32 is connected to the linear screws 140 through the carriage assembly 138. A linear bearing 150 is mounted to the carriage assembly 138 to provide additional support. The linear screws 140 are driven via the timing belt 144 which is coupled to a 24 volt DC motor 148. The motor control is based on force feedback from a piezoelectric sensor 36. Because, the linear screws 140 cause backdrive, the brake is needed to maintain the extraction vessel 16 in the clamping position.

The extraction chamber assembly 18 is essentially comprised of five components. These are the housing chamber 43, the heating elements 42, insulation 152, the piezoelectric sensor 36 and the end cap 56. The housing chamber 43 is comprised of two parts, end plug 56 and sheath 156. The end plug 56 is made of SS 316 and has the necessary profile and surface finish to form a seal with the seal of the extraction vessel 16. The end plug 56 is threaded into the top of the sheath 156. The sheath 156 is comprised of carbon steel to provide good thermal conductivity with a SS 316 liner 158 which is used for protection. The sheath 156 is threadingly engaged with the C-frame 142 so that it may be removed for cleaning. To remove the chamber 43 for cleaning, the cap containing the insulation 152 is removed and the chamber 43 casing unscrewed from the c-frame.

The plunger 32 is comprised of SS 316 and has the necessary profile and surface finish to seal member 103 with the seal of the extraction vessel 16. The plunger 32 is threaded into the plunger carriage 138 so that it may be removed easily for cleaning. The plunger 32 is connected to the supercritical fluid providing means 12 through a coiled tube 31 which provides it with the flexibility necessary during motion of the plunger 32.

At some time prior to operation of the SFE system 10, the computer 64 of the extraction system 10 is programmed with the appropriate parameters for controlling the fluid extraction system during each of the sample runs, as shown in Table 1. These parameters can include, for instance, sample order; temperature control including extraction temperature, restrictor temperature, trap desorbing temperature and collection temperature; supercritical fluid pressure; flowrate; modifiers volume or mole percent (if any); flushing fluid content; static or dynamic extraction selection; extraction timing, valve timing and switching; analyte collection conditions; desorbing solvent volume; desorbing solvent flowrate; vessel position number and fraction collector position number. All of this can be performed for each vessel or for each fraction of a vessel. For example, a vessel can be fractionated in up to 16 parts with each part (i.e. fraction) having a different set of the above parameters (with the exception of vessel size). In this manner, the computer 64 can automatically control the fluid extraction system to extract and collect analytes from a multitude of samples. Thus, a user can simply load the system with samples, program the computer 64 and collect the extracted analytes each within their own vial from a fraction collector carousel 66.

Figure 13A:
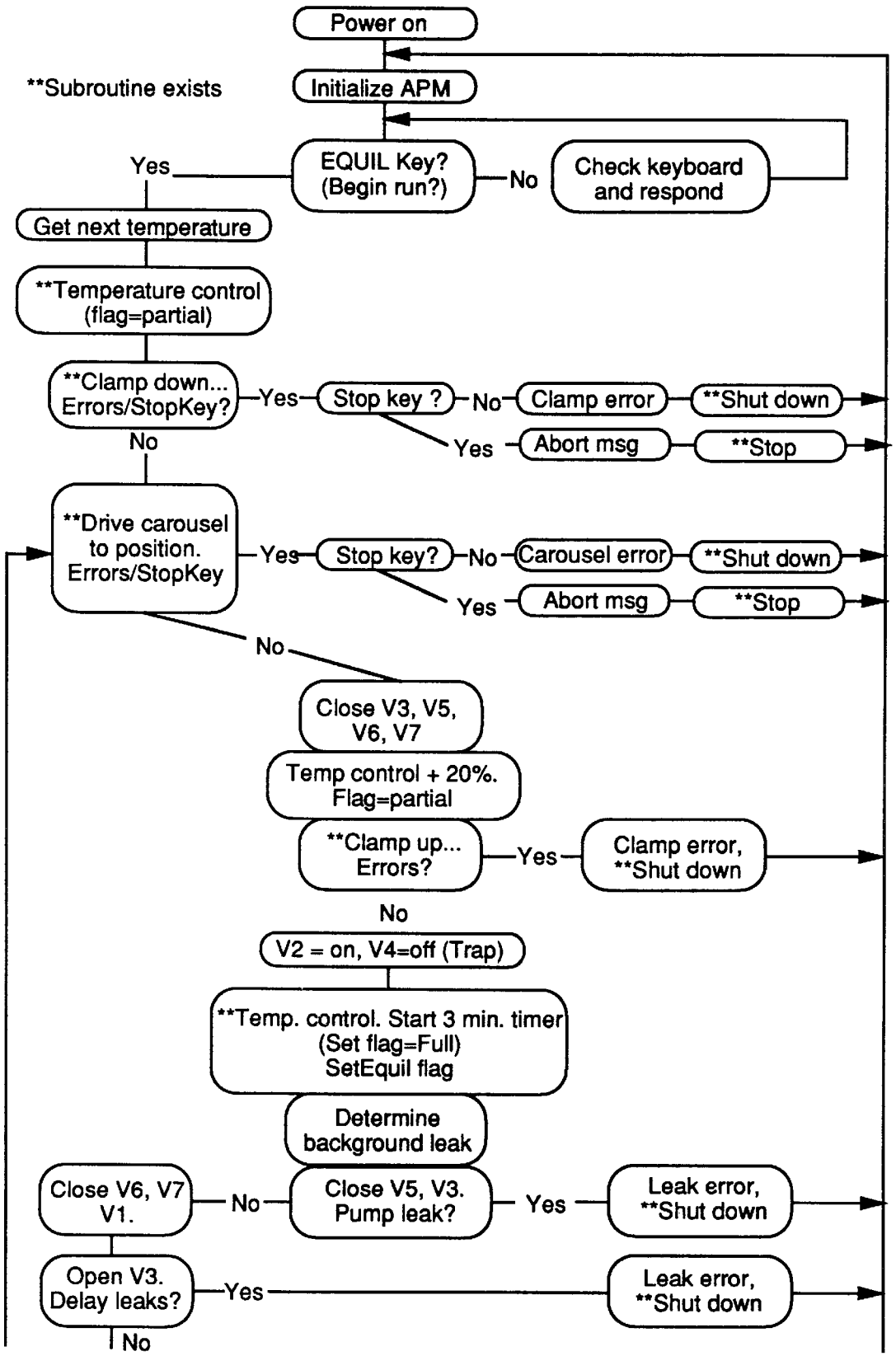
FIGS. 13a and 13B–C are flow chart representations of an algorithm followed by the computer during supercritical fluid extraction.
Figure 13B:
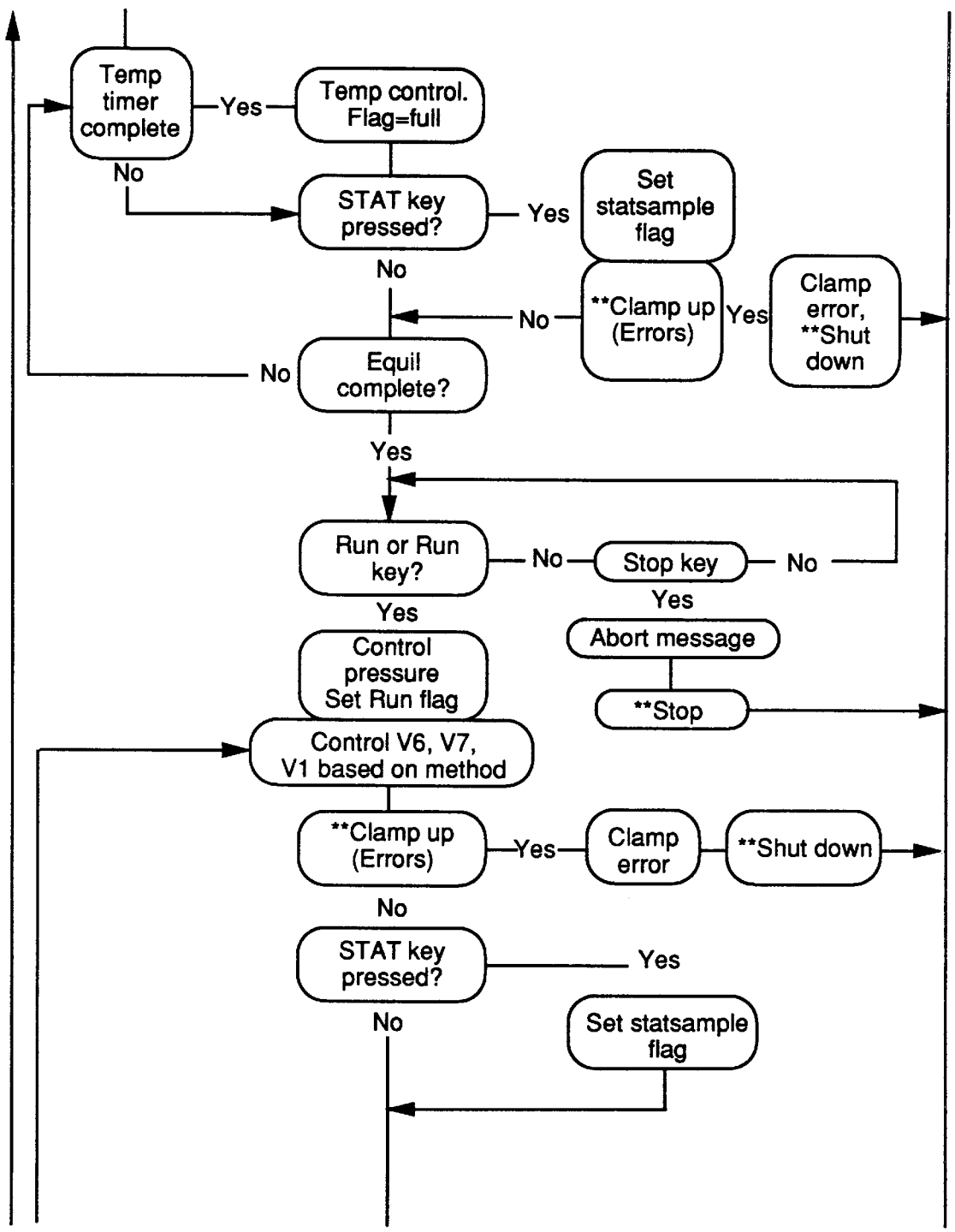
Figure 13C:
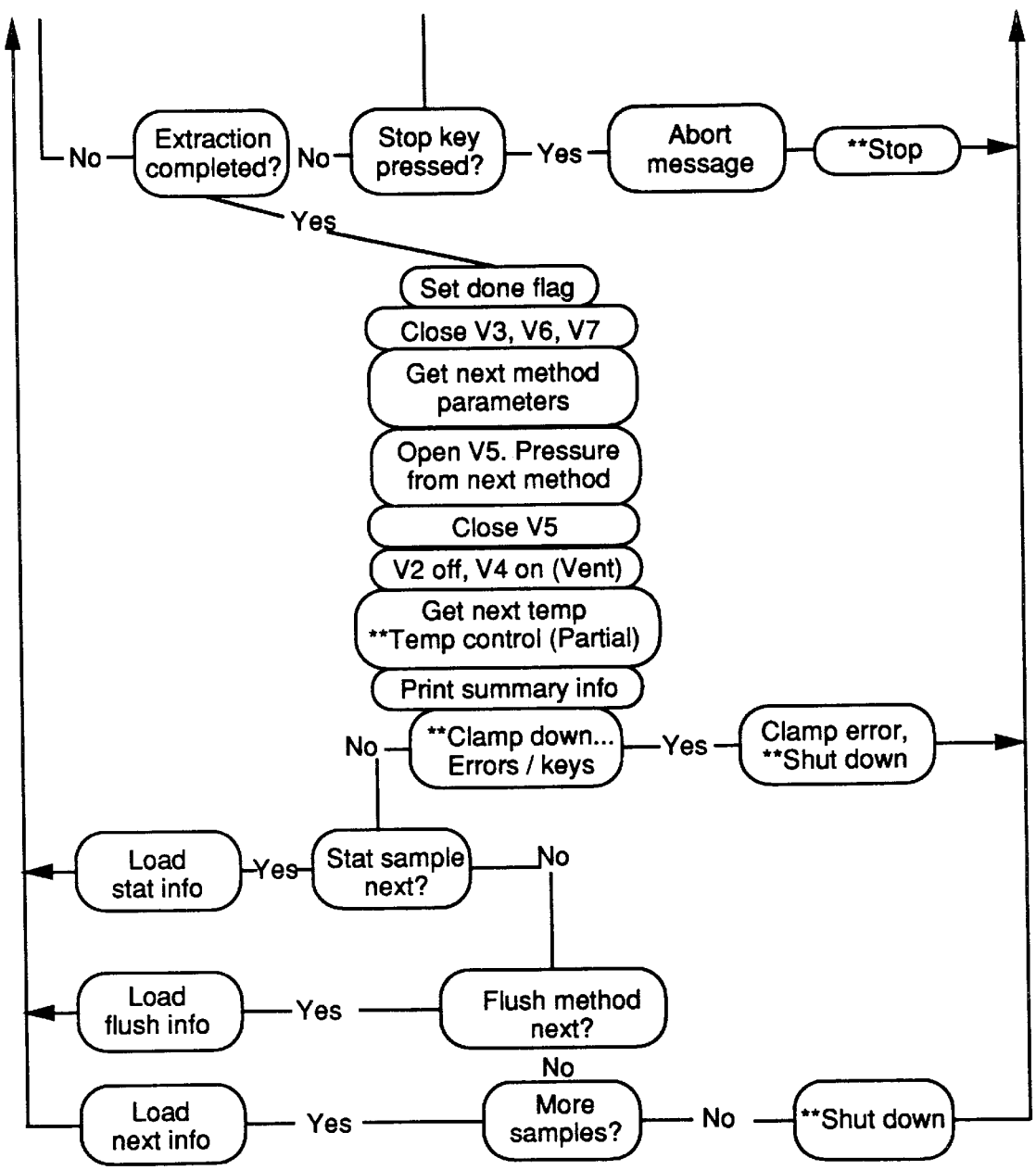

Once programmed, the extraction system 10 is activated by pushing a start button. The computer 64 then follows an algorithm which is summarized in flow chart form in FIGS. 13a and 13b. The computer 64 first controls the rotary table 30 and clamping mechanism 24 to position the blank extraction vessel 16 within the extraction chamber assembly 18. The valves of the SFE system 10 are selectively controlled while the SFE pump 126 supplies supercritical fluid in a manner which sequentially connects in stages the plumbing of the SFE system 10. By monitoring the action of the pump 126 during the specific stages, standard flow parameters can be derived which will be compared with the set flow parameter of 2.1 ml/min during extraction runs to detect plugs or leaks. Specifically, the computer 64 first closes valves V3 and V5 and reviews the action of the pump 126. Next, valves V6 and V7 and the static dynamic valve V1 are closed, and valve V3 is opened to allow the supercritical fluid to flow through the empty extraction vessel 16 up to the static dynamic valve V1. After a delay to allow the system 10 to fill and stabilize, the computer 64 again reviews the action of the pump 126. In this manner, standard flow parameters can be determined.

After determining the standard flow parameters of the SFE system 10, the empty vessel 16 is placed back into the carousel 28 and the computer 64 first retrieves the extraction temperature of the first sample to be extracted (65° C.) and controls the heating elements 42 within the extraction chamber assembly 18 accordingly. Next, the rotary table 30 is turned to a position where the extraction vessel 16 having the first sample to be extracted is in position between the extraction chamber assembly 18 and plunger 32. The computer 64 identifies the position of the rotary table 30 with a position encoder 160, as shown in FIG. 2.

The computer 64 controls the plunger 32 to move the first extraction vessel 16 into the extraction chamber assembly 18 which is now heated to the desired temperature of 65° C. to facilitate the solubilization of the analyte with the supercritical $CO_2$ and any modifier when it is introduced therewith. Nipples 108 on the plug 56 and plunger 32 press the respective check valves 96, 98 such that the seal portions 100 of the check valves 96, 98 are moved from their respective seal member 103 so that a fluid flow channel is opened for supercritical fluid to flow therethrough.

Then, the computer 64 checks for leaks and plugs within the fluid extraction system. The valves of the extraction system are selectively controlled while the pump 126 supplies the supercritical fluid in a manner which sequentially connects in stages the plumbing of the SFE system 10. The pump's 126 action is compared with the previously derived standards to ascertain if a leak or plug is present. For instance, if the flowrate is too large during a specific testing stage, a leak is identified and the user is notified via a display. Conversely, if the flow is too small during testing, a plug is identified and the user is notified via the display. By selectively controlling the valves to sequentially connect the downstream plumbing, the specific portion of plumbing which has a leak or a plug can be determined.

Specifically, the computer 64 first closes valves V3, V5 and reviews the action of the pump 126. Depending on the action of the pump 126 relative to the standards previously measured during testing with the empty vessel 16 indicates whether there is a plug or a leak between the pumping means and valves V5 and V3. Similarly, to test the SFE system 10 to valve V1, valve V3 is opened, and valves V6 and V7 are shut and after the system is allowed to stabilize with respect to the fluid filling the plumbing to additional valve V3, the action of the pump 126 is reviewed, again with respect to the previously determined standard. This automatic leak and plug detection is unique in the art of supercritical fluid extraction.

Assuming no leaks or plugs are detected during testing, the computer 64 retrieves information for the extraction parameters of the first run which were programmed previously, as shown in Table 1. Valve V1 is opened and valves V6 and V7 are selectively controlled to mix the appropriate modifiers with the supercritical $CO_2$ in the mixing tee 62. The supercritical $CO_2$ with the desired modifiers, if any, flows through the flexible coiled tubing 31 through the plunger 32 and into the extraction vessel 16 within the heated extraction chamber 16. Heating elements 38 within the plunger 32 preheat the supercritical $CO_2$ to 65° C. The maximum flowrate is 7 ml/min. at 680 atm.

In the extraction vessel 16, the supercritical $CO_2$ solubilizes analyte from the sample. The ultrasonic energy providing means 58 (a 20 kHz high power ultrasonic horn such as Bransen W-350 sonifier with a 102 converter) provides ultrasonic energy to the supercritical $CO_2$ and the sample to expedite the diffusion of analyte from the interior of the sample matrix to the surface of the sample matrix. The ultrasonic energy means 58 is controlled by the computer 64.

The analyte which is dissolved in the supercritical $CO_2$ at 100–680 and preferably 450 atmospheres and 40° C.–200° C. and preferably 65° C. temperature is provided to the restrictor 22 by way of 316 stainless steel tubing. The tubing passes through an in-line cup filter whose purpose is additional prevention of plugging or clogging of the restrictor 22. The supercritical fluid continues to flow at this time to act also as a transport to carry the analyte to the collection means 20. The supercritical fluid enters the first port 68 of the restrictor 22. Needle member 80 is positioned in the first port 68 and is selectively moved by a motor 82 which moves the needle member 80 via a gear 78. The computer 64 controls the motor 82.

Restrictor 22 is controlled to produce a flow of 2.1 ml/min. The flow through the restrictor 22 results in a corresponding pressure drop such that analyte dissolved in the supercritical $CO_2$ passes therethrough to the second port 70 of the restrictor 22 having a pressure of about 1–10 atmospheres. After the $CO_2$ with analyte passes through the restrictor 22, it is no longer supercritical but is now gaseous $CO_2$.

The second port 70 of the restrictor 22 is fluidically connected to a collection trap 164 by stainless steel tubing. The $CO_2$ with the analyte flows therethrough at a pressure of approximately 1 to 10 atmospheres. The restrictor 22 is maintained at 40° C. to 150° C. and preferably 150° C. with heating means such as a cartridge heater 162. A thermalcouple in thermal contact with the restrictor 22 senses the temperature of the restrictor 22 and controls the amount of heat provided thereto with the heating means 162. The heated restrictor 22 facilitates movement of fluid thereacross and minimizes its clogging and prevents freezing of the $CO_2$ in the second port 70 or collection means 20.

The collection trap 164 is made of PEEK, stainless and carbon steel for good heat transfer and is capable of withstanding pressures up to 65 atmospheres. The collection trap 164 has an inside diameter of 4.6 millimeters, a ¼ inch outside diameter and is 7.5 centimeters long. The collection trap 164 is filled with silanized glass beads of 100–120 mesh. The presence of the beads increases the surface area upon which analyte can solidify as it passes through the collection trap 164. During collection, the collection trap 164 is cryogenically cooled to −50° C. with cooling means 174 such as with liquid $CO_2$. The collection trap 164 is able to be cooled within a two-minute period from ambient temperature to −65° C. or any set temperature in-between. The cooling liquid $CO_2$ is provided by known techniques about the collection trap 164 and includes an on-off valve to deliver the cooling $CO_2$.

The analyte precipitates from the depressurized $CO_2$ into the collection trap 164. The $CO_2$ exits the collection trap 164 through the fraction collector 66, through the expanded gas flow meter 172 and to a vent.

During the extraction, V1 is in the static position for 5 minutes and in the dynamic position for 30 minutes. At the end of an extraction after 35 minutes, which the computer 64 can know based on elapsed time, the static/dynamic valve V1 switches such that the flow of supercritical fluid from the extraction vessel is shut off from the collection means 20 so that the desorbing means 74 can function properly. This results in a state where the extraction vessel 16 with sample is pressurized with supercritical $CO_2$ fluid. The supercritical fluid upstream of static/dynamic valve V1 must be vented from the extraction vessel 16 so that the extraction vessel 16 reaches atmospheric pressure. Then the vessel 16 can be removed from the extraction chamber assembly 18 and returned to the carousel 28 and the next vessel from the carousel 28 can be loaded into the extraction chamber 18 to begin the next extraction.

The venting of the remaining supercritical fluid in the system 10 occurs by: 1) closing valves V3, V6 and V7 between the fluid and modifier pumps 126, 127 and the extraction vessel 16 to isolate the source of the supercritical fluid and then, 2) opening the vent valve V2 and then V1 is opened for venting the fluid in the extraction vessel. This venting is controlled by the computer 64.

Meanwhile, the analyte within the collection trap 164 is desorbed with desorbing solvent such as methylene chloride by opening valve V11. The collection trap 164 is then ballistically heated from −50° C. to 30° C. within thirty seconds using an inductive heating coil 168. A liquid pump 170 of the device for providing desorbing solvent 74 is activated to cause the flow of desorbing solvent to the collection trap 164 through the third port 72 of the restrictor 22. As the desorbing solvent flows through the collection trap 164, the analyte dissolves in the desorbing solvent. The desorbing solvent flowrate is 0.5 ml/min for a 2 minute duration to produce 1.0 ml of total flow of desorbing solvent. The desorbing solvent continues through the collection trap 164 gathering analyte and flows via stainless steel tubing to a 2.0 ml vial within the fraction collector carousel 66. The position of the fraction collector carousel 66 is controlled by computer 64 such that a different vial is in fluidic communication with the collection trap during each extraction cycle. The fraction collector carousel 66 is cooled by a glycol/water cooling unit 112 to maintain the vials within a stable environment of 4° C.

In order to remove analytes that may remain in the downstream plumbing from the extraction vessel 16 to the collection means 20, the SFE system 10 is flushed. In this manner, the system is "clean" for the next sample extraction.

The system flushing is accomplished by loading the blank extraction vessel 16 in the carousel 28. The system 10 loads this blank vessel from the carousel 28 and into the extraction chamber assembly 18. The system 10 can then be programmed to deliver either 100% supercritical fluid, 100% modifier or a programmed combination of the two (supercritical fluid/modifier mixture) to the extraction system. In this case, 100% $CO_2$ was used.

This fluid is delivered from the pumps 126, 127, through the inlet tubing to the blank vessel 16 and through the downstream plumbing to the 4-port, 2-way switching valve V2. This valve can be switched so that the flush can either be directed into the collection means 20 to also clean it out of remaining analytes or to the vent to vent all of the flushing fluid.

This flushing allows the decontamination and cleaning of the extraction system 10. The flushing cycle is done automatically by the system 10 as programmed by the user and uses a pure modifier or a supercritical fluid-modifier mixture so that the polarity of the fluid used to clean the system 10 can be matched with the polarity of the analytes that contaminate the system 10.

The computer 64 prepares for the next run by opening the static/dynamic valve V1 and switching the vent valve V2 to allow fluidic communication between the extraction chamber assembly 18 and the collection trap 20. The carousel 28 is rotated to position the extraction vessel 16 of the second run between the plunger 32 and the extraction chamber assembly 18. The computer 64 then follows the algorithm of FIGS. 13a and 13b again. The heating elements 42 of the extraction chamber 18 are controlled accordingly and the extraction system 10 is tested for leaks and plugs. The computer 64 then controls the extraction system 10 with the programmed extraction parameters for extraction of the analyte from the second extraction vessel 16. At the end of the second run the analyte in the desorbing solvent is sent to a second vial of the fraction collector carousel 66.

Once all the sample have been extracted, the fraction collector carousel 66 having the filled vials of analyte is removed from the extraction system 10. The vials can then be loaded onto a liquid chromatograph or gas chromatograph or other analytical technique to determine their chemical content.

The result of the SFE extractions are shown in Table 2 where the SFE results are compared to Soxhlet extraction results for the SRS103-100 sample. In general, SFE provided improved recoveries with very good relative standard deviations (% RSD).

TABLE 2

Comparison of SFE Results with Soxhlet Extraction Results

| Analyte | Soxhlet Cartified PPM in Soil | | | SFE PPM | SFE Recovery | SFE % Relative Standard |
| | Minimum | Maximum | Average | Average | % | Deviation |
| --- | --- | --- | --- | --- | --- | --- |
| Naphthalene | 24.2 | 40.6 | 32.4 | 39.9 | 123% | 5.2% |
| Acenaphthylene | 14.7 | 23.5 | 19.1 | 46.3 | 242% | 6.2% |
| Acenaphthene | 527 | 737 | 632 | 533 | 84% | 1.0% |
| Fluorene | 414 | 570 | 492 | 401 | 82% | 1.3% |
| Phenanthrene | 1270 | 1966 | 1618 | 1419 | 88% | 1.2% |
| Anthracene | 373 | 471 | 422 | 473 | 112% | 7.0% |
| Fluoranthene | 1060 | 1500 | 1280 | 1165 | 91% | 1.3% |
| Pyrene | 774 | 1322 | 1048 | 1058 | 101% | 1.6% |
| Benzo(a)Anthracene | 214 | 290 | 252 | 249 | 99% | 3.6% |
| Chyrsene | 271 | 232 | 251.5 | 334 | 133% | 1.9% |
| Benzo(b)Fluoranthene | 130 | 174 | 152 | 160 | 105% | 6.0% |
| Benzo(k)Fluoranthene | 130 | 174 | 152 | 148 | 97% | 8.5% |
| Benzo(a)Pyrene | 80.1 | 114.3 | 97.2 | 174 | 179% | 12.0% |

Figure 16:
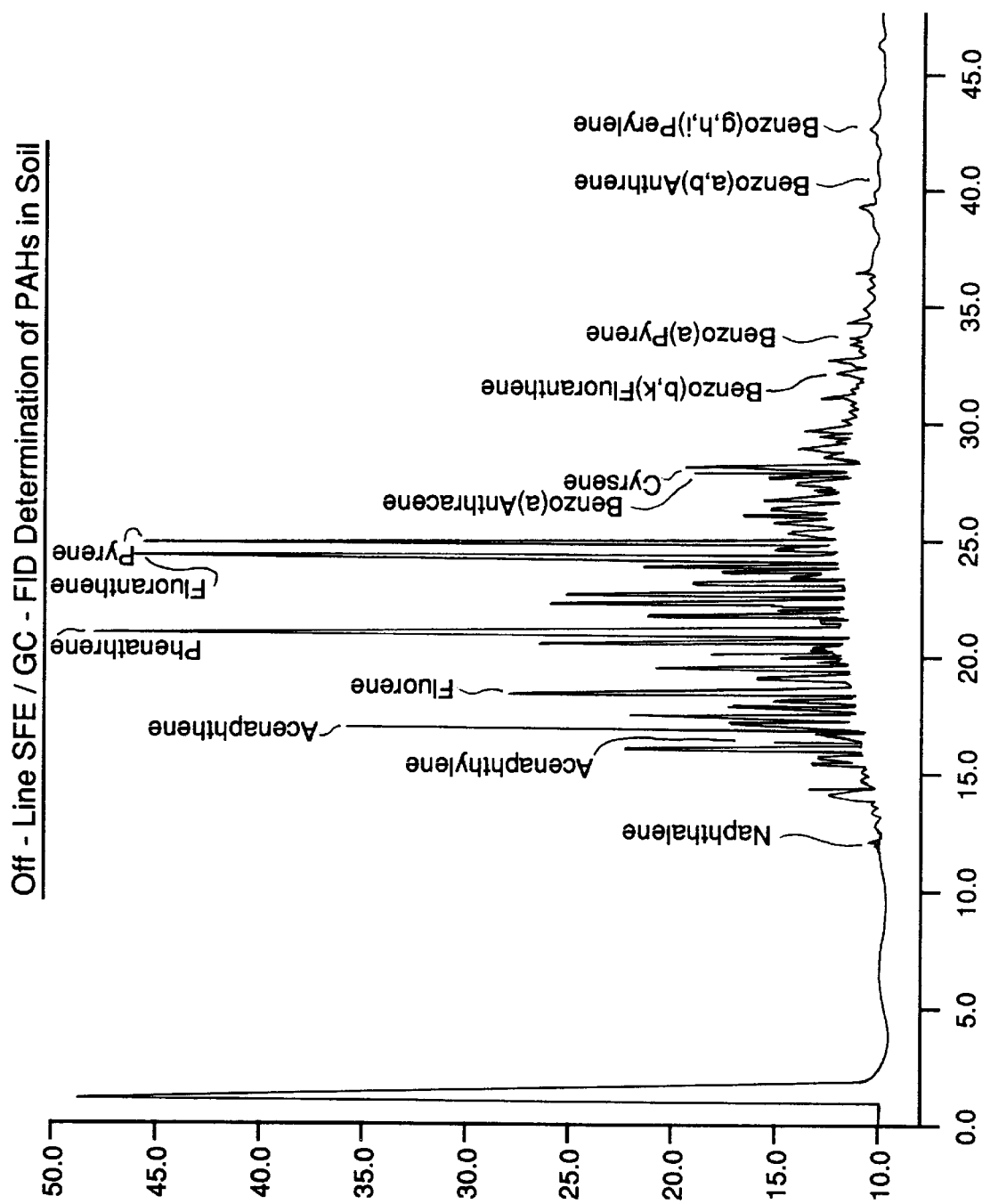
FIG. 16 is a graph of off-line SFE/GC-FID Determination of PAHs in soil.

Notes:
Soxhlet values certified by Resource Technology Corporation
SFE values average and % Relative standard deviation (% RSD) based upon 7 replicate extractions FIG. 16 reflects the gas chromatography results using a flare ionization detector of Run Number 1 of the SFE extractions.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A supercritical fluid extraction system comprising:
   means for providing supercritical fluid for extracting analyte from a sample;
   means for holding a plurality of extraction vessels having samples therein;
   an extraction chamber assembly;
   means for selectively moving an extraction vessel from the holding means into the extraction chamber assembly so supercritical fluid can flow through the extraction vessel and extract analyte from the sample and microprocessor means for individually programming each vessel with extraction process parameters.

2. A system as described in claim 1 wherein the microprocessor means includes a computer for automatically controlling the providing means, the holding means, the moving means and the extraction chamber assembly such that the analyte is extracted and collected at a desired pressure and a desired temperature with the desired supercritical fluid at a desired flow rate and a desired time, said computer in communication therewith.

3. A supercritical fluid extraction system as described in claim 2 including means for collecting analyte from the fluid with analyte, said collecting means in fluidic communication with the extraction chamber assembly.

4. A system as described in claim 3 wherein the extracting or collecting means includes a restrictor for controlling flow of fluid with analyte from a selected extraction vessel, said restrictor converting the fluid with analyte from a first supercritical pressure to a second pressure, said second pressure less than said first supercritical pressure.

5. A system as described in claim 4 including means for providing a modifier to the supercritical fluid, said modifier providing means in fluidic communication with said means for providing supercritical fluid.

6. A system as described in claim 5 wherein the collecting means includes a collection trap in which analyte is collected from the fluid and means for providing desorbing solvent to the collection trap which dissolves analyte therein.

7. A system as described in claim 6 including means for controlling flow of the fluid from the providing means to the extraction vessel and to the collecting means such that any leaks and plugs can be detected.

8. A system as described in claim 7 wherein the supercritical fluid providing means comprises a pumping system having an output from which supercritical fluid at a desired pressure and flowrate passes; a source tank of supercritical fluid, said source tank in fluidic communication with the output, said pumping means having at least one variable speed piston which pressurizes the fluid, the speed of the piston at a given time corresponding to the pressure and flowrate of the fluid which passes from the output at the given time; and microprocessor control means for controlling the pumping means such that the pressure and flowrate of the supercritical fluid provided by the output is maintained at a desired pressure and flowrate.

9. A system as described in claim 8 wherein the restrictor is an automated variable restrictor.

10. A system as described in claim 9 including a vent valve for venting fluid from the extraction vessel, said vent valve located downstream of said extraction vessel and in fluidic communication with said extraction vessel, said vent valve having a first path and a second path.

11. A system as described in claim 10 including plumbing which fluidically connects the supercritical providing means, the modifier providing means, the extraction chamber assembly, the moving means, the collection means and to the exit valve so a desired fluid can flow therebetween; and including means for flushing the plumbing, the moving means, the vent valve, and the collection means to cleanse the same.

12. A system as described in claim 11 wherein the moving means includes a mechanism for clamping an extraction vessel within the extraction chamber assembly such that the extraction vessel is disposed in fluidic communication between the supercritical fluid providing means and the collecting means; and means for presenting an extraction vessel from the holding means to the clamping mechanism so that the clamping mechanism can clamp an extraction vessel such that the extraction vessel is disposed between the supercritical fluid providing means and the collecting means, said presenting means disposed adjacent to said clamping mechanism.

13. A system as described in claim 12 wherein the holding means includes a carousel within which the plurality of extraction vessels are held, and the presenting means includes a rotary table in contact with the carousel for turning the carousel to selectively present the extraction vessels to the clamping mechanism.

14. A system as described in claim 13 wherein the clamping mechanism includes a plunger in fluidic communication with the means for providing supercritical fluid; and means for driving the plunger such that an extraction vessel presented to the plunger by the presenting means can be pushed from the carousel by the plunger into the extraction chamber assembly.

15. A system as described in claim 14 including means for sensing when a selected extraction vessel is in proper engagement within the extraction chamber assembly, said sensing means in electronic communication with the means for driving the plunger.

16. A system as described in claim 15 wherein the extraction chamber assembly includes means for heating the extraction vessel within the extraction chamber assembly, said heating element in thermal communication with an extraction vessel in said chamber assembly.

17. A system as described in claim 16 wherein the plunger or extraction chamber inlet includes means for preheating the supercritical fluid as it flows therethrough.

18. A system as described in claim 17 wherein the extraction vessels are adapted to withstand the pressure of the supercritical fluid.

19. A system as described in claim 18 wherein the holding means comprises means for cooling the extraction vessels within the holding means, said cooling means in thermal communication with the holding means.

20. A system as described in claim 19 wherein the extraction chamber assembly includes means for providing ultrasonic energy to an extraction vessel within the extraction chamber assembly, said ultrasonic means in communication with an extraction vessel within the extraction chamber assembly.

21. A system as described in claim 20 wherein the extraction vessel is comprised of:
   a container having a chamber, a first end having a first opening in fluidic communication with the chamber and a second end having a second opening in fluid communication with the chamber;
   a first check valve disposed on the first end of the container for selectively sealing the first opening from the chamber; and a second check valve disposed on the second end of the container for selectively sealing the second opening from the chamber.

22. A system as described in claim 21 wherein each of the check valves is comprised of a seal portion and a spring portion in contact with the seal portion for biasing the seal portion against the respective opening.

23. A system as described in claim 22 wherein the controlling means comprises a plurality of valves for controlling the flow of fluid therethrough, said controlling means selectively controlling the valves and monitoring flow of the fluid through the valves in order to detect and identify leaks and plugs.

24. A system as described in claim 23 wherein the collecting means includes means for heating the collection trap, said heating means in thermal communication with the collection trap; and means for cooling the collection trap, said means in thermal communication with the collection trap.

25. A system as described in claim 24 wherein the collection means includes at least a first vial in fluidic communication with the collection trap to which analyte dissolved in the desorbing fluid flows.

26. A system as described in claim 25 wherein the collection means includes a cooling unit which maintains the vial at a desired temperature, said cooling unit disposed adjacent to and in thermal communication with the vial.

27. A system as described in claim 26 wherein the collection means includes a fraction collector carousel in which the first vial and at least a second vial, said fraction collection carousel in communication with the computer which controls the position of the fraction collection carousel so a desired vial is positioned to receive desorbing fluid with dissolved analyte at a desired time, said cooling unit maintaining the fraction collection carousel at a desired temperature.

28. A system as described in claim 27 including means for removing water from the supercritical fluid with analyte, said water removing means in fluidic communication with the extraction chamber assembly.

29. A system as described in claim 28 wherein the water removing means includes an absorbent vessel in fluidic communication with the extraction vessel, said absorbent vessel having a material for absorbing water as the supercritical fluid with analyte flows therethrough, said water removing means in fluidic communication with the extraction vessel.

30. A system as described in claim 17 wherein the extraction chamber assembly has pressure retaining means able to withstand pressure up to 680 atm, and an extraction vessel within the extraction chamber assembly is contained by the pressure retaining means, said extraction vessel made of a material not able to independently withstand pressure greater than 50 atm, said vessel when disposed within the pressure retaining means and transmitting pressure therein to the pressure retaining means.

31. A system as described in claim 30 wherein the pressure retaining means is comprised of a first half and a second half which are hingeably connected to form a closed pressure chamber which holds the vessel when they are in contact, and release the vessel when they are not in contact.

32. A system as described in claim 17 wherein the extraction chamber assembly has pressure retaining means able to withstand pressure up to 680 atm, and an extraction vessel within the extraction chamber assembly is contained by the pressure retaining means, said extraction vessel made of a material not able to independently withstand pressure greater than 50 atm.

33. A system as described in claim 32 wherein the extraction vessel is porous.

34. A system as described in claim 33 wherein the vessel is made of teflon, PEEK, stainless steel, plastic or paper.

35. A system as described in claim 15 including high power heating means for heating the supercritical fluid to appropriate extraction temperature conditions before the supercritical fluid enters the extraction vessel, said high power heating means in thermal communication with an inlet to the extraction vessel.

36. A system as described in claim 35 wherein the extraction chamber assembly has thermal insulation to retain heat in the supercritical fluid when it enters the extraction chamber assembly to solubilize analyte in the matrix therein.

37. A system as described in claim 9 wherein the automated variable restrictor defines a channel therethrough, a portion of said channel having a variable inner diameter, and wherein the supercritical fluid includes modifier concentrations as great as 50%, said variable inner diameter of said channel adaptable to allow the fluid through the channel without clogging.

38. A system as described in claim 37 wherein the computer monitors flow of fluid through the channel and varies the diameter of the portion of the channel based on the flow of fluid through the channel.

39. A system as described in claim 38 wherein the automated variable restrictor has a maximum dead volume of 0.86 microliters.

40. An extraction vessel for use with supercritical fluid extraction comprising:
  a container having a chamber, a first end having a first opening in fluidic communication with the chamber and a second end having a second opening in fluid communication with the chamber;
  a first check valve disposed on the first end of the container for selectively sealing the first opening from the chamber; and
  a second check valve disposed on the second end of the container for selectively sealing the second opening from the chamber, said container with the first check valve disposed on the first end and the second check valve disposed on the second end constructed and designed to contain fluid at supercritical temperatures and pressures.

41. An extraction vessel as described in claim 40 wherein each of the check valves is comprised of a seal portion and a spring portion in contact with the seal portion for biasing the seal portion against the respective opening.

42. An extraction vessel as described in claim 41 wherein each end of the container comprises a seal member defining the first and second openings, respectively, and each of the seal portions are spring biased against the respective seal member.

43. An extraction vessel for use with supercritical fluid extraction comprising:
  a container having a chamber, a first end having a first opening in fluid communication with the chamber and a second end having a second opening;
  a first breakable membrane sealing the first opening; and
  a second breakable membrane sealing the second opening, said container with the first membrane sealing the first opening and with the second membrane sealing the second opening constructed and designed to contain fluid at supercritical temperatures and pressures.

44. An extraction vessel as described in claim 43 wherein the first and second membranes have a plurality of channels such that the first and second membranes fracture along the channels during puncturing of the first and second membranes.

45. An extraction vessel as described in claim 44 wherein the first and second membranes are comprised of teflon or PEEK material.

46. A system for supercritical fluid extraction comprising:
   means for providing supercritical fluid for extracting analyte from a sample;
   an extraction vessel having a sample therein, said extraction vessel in fluidic communication with the providing means such that supercritical fluid is provided to the extraction vessel to transfer analyte therefrom;
   a vent valve for venting fluid from the extraction vessel to atmosphere, said vent valve located downstream of said extraction vessel and in fluidic communication with said extraction vessel, said vent valve having a first path and a second path; and
   means for collecting analyte from the fluid, said collecting means in fluidic communication with the extraction vessel through the first path, said fluid vented from the extraction vessel away from the collection means along the second path.

47. A system as described in claim 46 including a computer for automatically controlling the vent valve.

48. A method for supercritical fluid extraction comprising the steps of:
   extracting analyte from an extraction vessel with supercritical fluid;
   collecting analyte from the supercritical fluid in a collection trap in fluidic communication with the extraction vessel; and
   venting to atmosphere the supercritical fluid from the extraction vessel from a location downstream of the extraction vessel but upstream of the collection trap.

49. A method as described in claim 48 wherein the venting step includes the step of automatically controlling a vent valve with a computer.

50. A supercritical fluid extraction system comprising:
   means for providing supercritical fluid for extracting analyte from a sample;
   an extraction vessel having a sample therein, said extraction vessel in fluidic communication with the providing means such that supercritical fluid is provided to the extraction vessel to transfer analyte therefrom;
   means for collecting analyte from the fluid, said collecting means in fluidic communication with the extraction vessel; and
   means for controlling flow of the fluid from the providing means to the extraction vessel and to the collecting means such that any leaks and plugs can be detected.

51. A system as described in claim 50 wherein the controlling means comprises a plurality of valves for controlling the flow of fluid therethrough, said controlling means selectively controlling the valves and monitoring flow of the fluid through the valves in order to detect and identify leaks and plugs.

52. A system as described in claim 51 wherein the controlling means includes a computer which controls which valve is open or closed at a given time and monitors fluid flow.

53. An extraction system for supercritical fluid extraction comprising:
   an extraction chamber assembly for extracting analyte from a sample with supercritical fluid; and
   means for removing water from the supercritical fluid with analyte, said water removing means in fluidic communication the extraction chamber assembly.

54. An extraction vessel as described in claim 53 wherein the extracting means includes an extraction vessel having the sample within and the water removing means includes an absorbent vessel in fluidic communication with the extraction vessel having a material for absorbing water as the supercritical fluid with analyte flows therethrough, said water removing means in fluidic communication with the extraction vessel.

55. An extraction system as described in claim 54 wherein the material comprises sodium sulfate or magnesium sulfate.

56. An extraction system as described in claim 55 wherein the material is comprised of hydromatrix, a form of diatomaceous earth.

57. An extraction device for use with supercritical fluid extraction comprising:
   an insert constructed and arranged for holding a sample, said insert being porous; and
   a container having a chamber which contains the insert, said container operable to retain the pressure of the supercritical fluid within the insert.

58. An extraction device as described in claim 57 including means for providing supercritical fluid to the insert such that analyte can be extracted from the sample within the insert, said providing means in fluidic communication the insert.

59. An extraction system as described in claim 58 wherein the insert is made of teflon, PEEK, stainless steel, plastic or paper.

60. A system for use with supercritical fluid extraction comprising:
   means for extracting analyte from a sample with supercritical fluid;
   means for collecting analyte from the fluid; said collecting means in fluidic communication with the extracting means;
   means for providing desorbing solvent to the collecting means, said desorbent providing means in fluidic communication with the collecting means; and
   a restrictor for controlling flow of fluid with analyte from the extracting means to the collecting means, said restrictor having a first port in fluidic communication with the extracting means, a second port in fluidic communication with the collecting means and a third port in fluid communication with desorbing providing means, said restrictor having a needle member and means for selectively moving the needle member such that the fluid with analyte is converted from a first supercritical pressure in the first port to a second pressure in the second port which is less than the first pressure; and
   a computer for automatically controlling the moving means, said computer in communication with the moving means.

61. A restrictor as described in claim 60 including a body member having the first, second and third ports, said body member having a maximum dimension less than 1 inch and a dead volume of less than 1 microliter.

62. A restrictor as described in claim 61 wherein the needle member has a diameter of less than $1/16$ of an inch.

63. A restrictor as described in claim 62 including a seat member disposed in the first, said seat member having a length less than 0.3 inches, said seat member having an internal diameter less than 0.016 inches, said seat member made of poly-ether-ether-ketone.

64. A restrictor as described in claim 63 having a total assembled length of less than 2.5 inches and having a total assembled width of less than 1.5 inches.

65. A restrictor as described in claim 60 wherein the selectively moving means moves the needle member based on flow rate of fluid between the first port and the second port.

66. A restrictor as described in claim 65 wherein the supercritical fluid includes modifier concentrations as great as 50% and the moving means moves the needle member to allow the fluid to pass between the first and second ports without clogging.

67. A pumping system for providing supercritical fluid comprising:

an output from which supercritical fluid at a desired pressure and flowrate passes;

means for providing supercritical fluid to the output, said providing means in fluidic communication with the output, said providing means having at least one variable speed piston which pressurizes the fluid, the speed of the piston at a given time corresponding to the pressure and flowrate of the fluid which passes from the output at the given time; and microprocessor control means for controlling the providing means such that the pressure and flowrate of the supercritical fluid provided by the output is maintained at a desired pressure and flowrate.

68. A pumping system as described in claim 67 wherein the providing means includes a source tank, a pump assembly having the piston in fluid communication with the source tank and a motor for driving the piston, said motor having a variable power input which is controlled by said microprocessor control means.

69. A pumping system as described in claim 68 wherein microprocessor control means includes a pressure transducer for measuring the pressure of the supercritical fluid at the output, said pressure transducer in fluidic communication with the output.

70. A pumping system as described in claim 69 wherein the microprocessor control means comprises a piston position potentiometer.

71. A pumping system as described in claim 70 wherein the output comprises a damping chamber which maintains the fluid passing therefrom essentially at a constant pressure.

72. A pumping system as described in claim 71 wherein the pump assembly comprises means for providing rotary motion, and means for converting the rotary motion into linear motion to drive the piston.

73. A pumping system as described in claim 72 wherein the rotary motion providing means comprises a pully and belt system connected to the motor and a crankshaft connected to the pulley system.

74. A pumping system as described in claim 73 wherein the means for converting the rotary motion into linear motion comprises a crank arm which is connected to the crankshaft at a first end and the piston at a second end.

75. An extraction system for supercritical fluid extraction comprising:

an extraction vessel having a sample therein; and means for providing supercritical fluid to the extraction vessel so that supercritical fluid can flow through the extraction vessel and extract analyte from the sample, said providing means including means for heating the supercritical fluid to a desired extraction temperature before the supercritical fluid enters the extraction vessel, said supercritical fluid heating means is disposed within a plunger or inlet to the extraction vessel which moves the extraction vessel into fluidic communication with the extraction system for supercritical fluid extraction.

76. A method for supercritical fluid extraction comprising the steps of:

moving an extraction vessel having a sample from a carousel having a plurality of extraction vessels each having a sample with an automated moving device into fluidic communication with a supercritical fluid extraction system so that the supercritical fluid can flow through the extraction vessel and extract analyte from the sample;

extracting analyte from the sample with supercritical fluid and providing a microprocessor means for individuallly programming each vessel with extraction process parameters.

77. A method as described in claim 76 wherein after the step of extracting analyte, there is the step of collecting analyte from the fluid.

78. A method as described in claim 77 wherein after the collecting step, there is the step of analyzing the analyte with a liquid or gas chromatograph.

79. A method as described in claim 78 wherein the extracting analyte step includes the step of extracting analyte from a sample with supercritical fluid under automated control by the supercritical fluid extraction device.

80. A supercritical fluid extraction system comprising:

means for providing supercritical fluid for extracting analyte from a sample;

means for holding a plurality of extraction vessels each having a sample therein;

means for selectively moving an extraction vessel from the holding device into fluid communication with the supercritical fluid providing means so that supercritical fluid can flow through said extraction vessel and gather analyte from the sample.

81. A supercritical fluid extraction device as described in claim 80 including means for collecting analyte from the fluid with analyte, said collecting means in fluidic communication with the extraction vessel.

82. A system for supercritical fluid extraction comprising:

an extraction chamber assembly in which a sample matrix with analyte has the analyte solubilized with supercritical fluid;

means for collecting the analyte, said collecting means connected to the extraction chamber assembly through plumbing;

means for providing supercritical fluid to the extraction chamber and connected thereto with plumbing;

means for providing modifier to the extraction chamber assembly and connected thereto with plumbing; and means for flushing the plumbing, extraction chamber assembly and collecting means with a desired fluid to cleanse it.

83. A system as described in claim 82 wherein the flushing means includes a blank vessel which, when disposed in the extraction chamber assembly, allows desired fluid to flow therethrough and cleanse the plumbing and collecting means; and including a computer connected to the modifier providing means and the supercritical fluid providing means for controlling the same such that the desired fluid flushing is obtained.

84. An apparatus for collecting analyte from supercritical fluid extraction comprising:

a collection trap in which analyte is collected;

means for providing desorbing fluid to the collection trap which dissolves the analyte therein, said desorbing providing means connected to the collection trap;

a fraction collection carousel having a first vial and at least a second vial, said fraction collection carousel in fluidic communication with the collection trap so desorbing fluid with dissolved analyte is received by a desired vial; and a computer in communication with the fraction collection carousel to position so a desired vial is in place to receive the desorbing fluid with dissolved analyte, and in communication with the desorbing fluid providing means to cause the desorbing fluid providing means to provide a desired desorbing fluid at a desired time.

85. An apparatus as described in claim 84 including a cooling unit which maintains the fraction collection carousel at a. desired temperature, said cooling unit disposed adjacent to and in thermal communication with the fraction collection carousel.

86. An extraction chamber assembly comprising:

pressure retaining means comprised of a first half and a second half which are hingeably connected to form a closed pressure chamber in which pressure up to 680 atm can be supported, said chamber receiving an extraction vessel holding a sample matrix, said chamber holds the vessel when they are in contact, and releases the vessel when they are not in contact; and means for heating the chamber, said heating means in thermal communication with the chamber and adjacent the pressure retaining means.

87. A system for supercritical fluid extraction comprising:

an extraction chamber assembly in which a sample matrix with analyte has the analyte solubilized with supercritical fluid;

means for collecting the analyte, said collecting means connected to the extraction chamber assembly through plumbing;

means for providing supercritical fluid to the extraction chamber and connected thereto with plumbing; and means for automatically controlling operation of the extraction chamber assembly, the collecting means and the providing means such that the analyte is extracted and collected at a desired pressure and a desired temperature with the desired supercritical fluid at a desired flow rate at a desired time, said controlling means in communication with the extraction chamber assembly, the collecting means and the providing means.

88. A supercritical fluid extraction system comprising:

a carousel for holding a plurality of extraction vessels, each extraction vessel having a sample;

an extraction chamber disposed adjacent to the carousel;

a mechanism for moving an extraction vessel from the carousel to the extraction chamber, said moving mechanism in communication with the carousel and the extraction chamber;

a pump for pumping supercritical fluid to the extraction vessel in the extraction chamber to extract analyte from the sample;

a variable restrictor for reducing the pressure of the supercritical fluid, said variable restrictor connected to the extraction chamber and microprocessor means for individually programming each vessel with extraction process parameters.

89. A method for extracting analyte comprising the steps of:

moving an extraction vessel having a sample from a plurality of extraction vessels each having samples with a moving mechanism;

placing the extraction vessel into an extraction chamber;

introducing supercritical fluid to the extraction vessel to extract analyte from the sample;

flowing the supercritical fluid from the extraction chamber through a variable restrictor to reduce the pressure of the supercritical fluid and providing a microprocessor means for individually programming each vessel with extraction process parameters.

90. A method as described in claim 89 wherein the flowing step includes the steps of:

flowing the supercritical fluid through a channel to reduce the pressure of the supercritical fluid; and varying the diameter of the channel to maintain a desired flow of the supercritical fluid through the channel.

91. An extraction apparatus comprising:

a mechanism for automatically performing supercritical fluid extraction on a series of samples one after the other without substantially handling the apparatus for supercritical fluid extraction between extractions;

said mechanism for automatically performing supercritical fluid extractions including:

an extraction chamber assembly having an interior, an exterior, an orifice for introduction of sample, a first port for fluid entrance and at least a second port for a fluid outlet;

a sample injector mechanism for automatically injecting into the extraction chamber assembly a series of samples from a storage apparatus for feeding samples in series and for extracting each sample prior to introducing the next sample; and a variable restrictor for reducing pressure of supercritical fluid after extraction has occurred in the extraction chamber assembly and microprocessor means for individually programming each vessel with extraction process parameters.

92. A method for supercritical fluid extraction of a sample comprising the steps of:

extracting under supercritical conditions by:

automatically injecting a series of samples into an extraction chamber assembly having an interior, an exterior, an orifice for introducing of sample, a first port for fluid entrance and at least a second port for a fluid outlet;

extracting each sample prior to introducing a next sample with solvent at a supercritical pressure;

flowing the fluid at the supercritical pressure through a variable restrictor to reduce the pressure and providing a microprocessor means for individually programming each vessel with extraction process parameters.

* * * * *